United States Patent
Han et al.

(10) Patent No.: US 10,779,768 B2
(45) Date of Patent: Sep. 22, 2020

(54) ELECTRONIC DEVICE AND CONTROL METHOD THEREOF

(71) Applicant: LG ELECTRONICS INC., Seoul (KR)

(72) Inventors: Jongbeom Han, Seoul (KR); Jongseok Park, Seoul (KR); Jaewon Han, Seoul (KR); MinJong Lee, Seoul (KR); Mijin Park, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 1256 days.

(21) Appl. No.: 14/966,583

(22) Filed: Dec. 11, 2015

(65) Prior Publication Data

US 2016/0278705 A1    Sep. 29, 2016

(30) Foreign Application Priority Data

Mar. 25, 2015  (KR) .................... 10-2015-0041827

(51) Int. Cl.
| | |
|---|---|
| *A61B 5/04* | (2006.01) |
| *A47K 13/00* | (2006.01) |
| *A61B 5/00* | (2006.01) |
| *A61B 5/053* | (2006.01) |
| *H04M 1/725* | (2006.01) |

(Continued)

(52) U.S. Cl.
CPC .......... *A61B 5/6887* (2013.01); *A61B 5/0002* (2013.01); *A61B 5/0077* (2013.01); *A61B 5/02055* (2013.01); *A61B 5/04085* (2013.01); *A61B 5/053* (2013.01); *A61B 5/0537* (2013.01); *A61B 5/1032* (2013.01); *A61B 5/4872* (2013.01); *A61B 5/4878* (2013.01); *H04M 1/7253* (2013.01); *A61B 5/01* (2013.01); *A61B 5/6844* (2013.01); *A61B 5/6898* (2013.01);

(Continued)

(58) Field of Classification Search
CPC . A61B 5/0006; A61B 5/0024; A61B 5/04085; A61B 2562/04; A61B 5/01; A61B 5/0402; A61B 5/0408; A61B 5/05; Y10T 24/44017; Y10T 24/44034; Y10T 24/44573; A47K 13/10; A47K 13/242
USPC ........................................ 600/372, 382–393
See application file for complete search history.

(56) References Cited

U.S. PATENT DOCUMENTS 3,431,004 A * 3/1969 Schell .................. A47K 13/242
292/258
4,536,926 A * 8/1985 Pantaleo .............. A63C 11/021
211/70.5

(Continued)

FOREIGN PATENT DOCUMENTS

| CN | 103924648 A | 7/2014 |
| CN | 104323770 A | 2/2015 |

(Continued)

*Primary Examiner* — Eun Hwa Kim
*Assistant Examiner* — Brian M Antiskay
(74) *Attorney, Agent, or Firm* — Dentons US LLP

(57) ABSTRACT

Disclosed are an electronic device and method for controlling the same. According to the present invention, an electronic device and method for controlling the same include a body, a plurality of electrodes exposed to a surface of the body to contact at least two portions of a user's body, and a controller configured to apply a current to at least any one of the plurality of electrodes to obtain a bio signal of the user. According to the present invention, the user's bio signal may be obtained.

5 Claims, 23 Drawing Sheets

(51) Int. Cl.
*A61B 5/0205* (2006.01)
*A61B 5/0408* (2006.01)
*A61B 5/103* (2006.01)
*A61B 5/01* (2006.01)

(52) U.S. Cl.
CPC . *A61B 2560/0468* (2013.01); *H04M 2250/12* (2013.01)

(56) References Cited

U.S. PATENT DOCUMENTS

| | | | | |
|---|---|---|---|---|
| 5,027,472 | A | * | 7/1991 | Goodman ............ A47K 13/105 16/422 |
| 5,111,539 | A | * | 5/1992 | Hiruta ................ A61B 5/02241 4/301 |
| 8,689,367 | B2 | * | 4/2014 | Nguyen ............... A47K 13/105 4/246.1 |
| 2003/0216665 | A1 | | 11/2003 | Masuo et al. |
| 2005/0182333 | A1 | * | 8/2005 | Nagata ................. A61B 5/0432 600/509 |
| 2005/0261605 | A1 | | 11/2005 | Shemer et al. |
| 2013/0211291 | A1 | * | 8/2013 | Tran .................... G06F 19/3418 600/595 |
| 2013/0263368 | A1 | | 10/2013 | Nguyen |

FOREIGN PATENT DOCUMENTS

| | | | |
|---|---|---|---|
| GB | 2109048 | * | 5/1983 |
| JP | 2000-333924 A | | 12/2000 |
| JP | 2002136497 A | | 5/2002 |
| JP | 2002224076 A | | 8/2002 |
| JP | 2009-270951 A | | 11/2009 |
| KR | 1020080037305 A | | 4/2008 |

* cited by examiner

20, Type A

20, Type B (a)

(b)

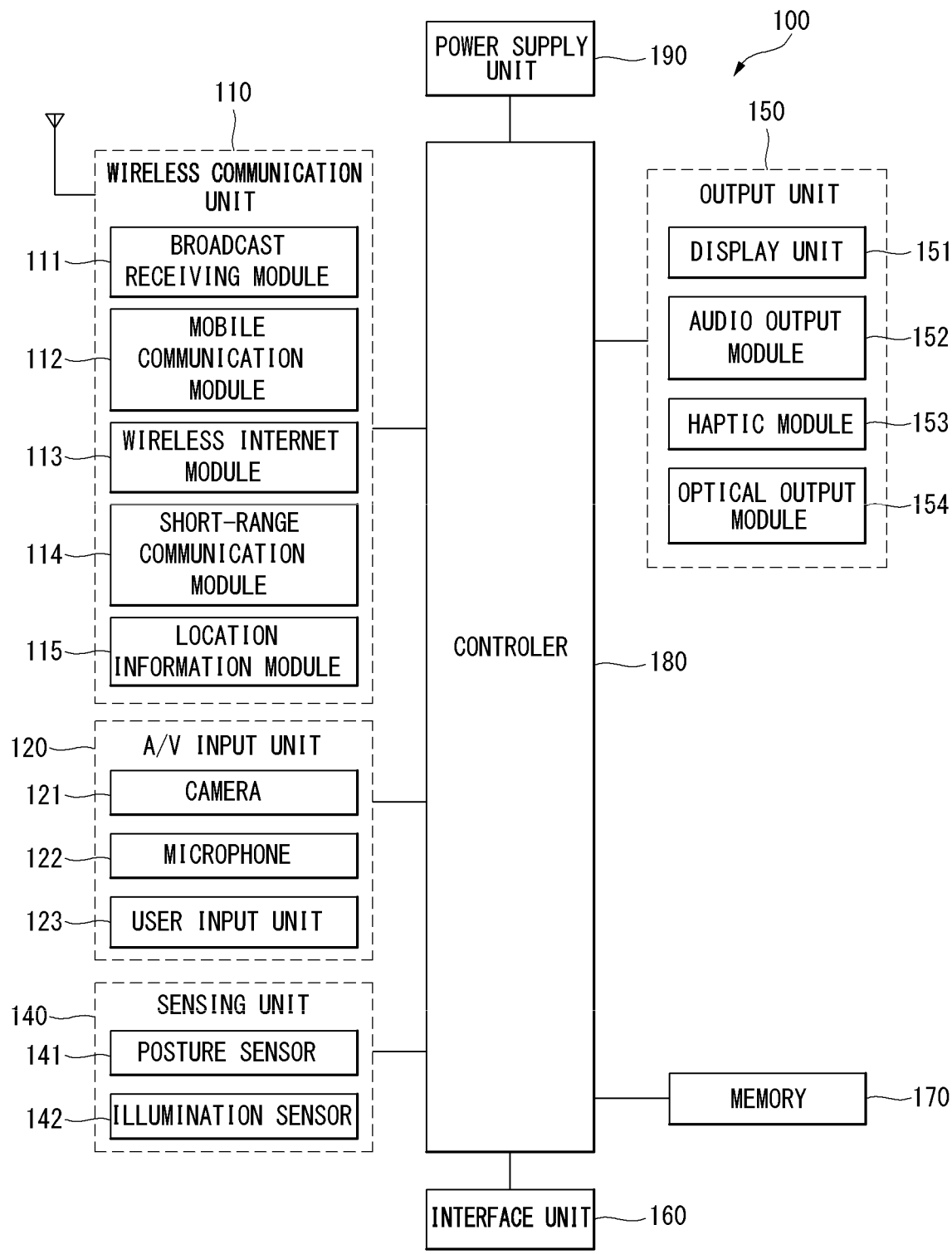

ELECTRONIC DEVICE AND CONTROL METHOD THEREOF

CROSS-REFERENCE TO RELATED APPLICATIONS

Pursuant to 35 U.S.C. § 119(a), this application claims the benefit of earlier filing date and right of priority to Korean Patent Application No. 10-2015-0041827, filed on Mar. 25, 2015, the contents of which are incorporated by reference herein in their entirety.

TECHNICAL FIELD

The present invention relates to electronic devices and methods for controlling the same, and more specifically, to electronic devices that may obtain users' bio signals and methods for controlling the same.

DISCUSSION OF THE RELATED ART

As functions of terminals such as personal computers, laptop computers, cellular phones diversify, the terminals become multimedia players having multiple functions for capturing pictures or moving images, playing music, moving image files and games and receiving broadcasting programs.

Terminals can be categorized as mobile terminals and stationary terminals. The mobile terminals can be further comprised of handheld terminals and vehicle mount terminals according to whether users can personally carry the terminals. Conventional terminals including mobile terminals provide an increasing number of complex and various functions.

To support and enhance the increasing number of functions in a terminal, improving a structural part and/or a software part of the terminal would be desirable.

SUMMARY

The present invention relates to electronic devices that may obtain users' bio signals and methods for controlling the same.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention.

FIG. 23 is a block diagram of a mobile terminal according to an embodiment.

DETAILED DESCRIPTION

Arrangements and embodiments may now be described more fully with reference to the accompanying drawings, in which exemplary embodiments may be shown. Embodiments may, however, be embodied in many different forms and should not be construed as being limited to embodiments set forth herein; rather, embodiments may be provided so that this disclosure will be thorough and complete, and will fully convey the concept to those skilled in the art.

A mobile terminal may be described below with reference to the accompanying drawings. In the following description, suffixes "module" and "unit" may be given to components of the mobile terminal in consideration of only facilitation of description and do not have meanings or functions discriminated from each other.

The mobile terminal may include a cellular phone, a smart phone, a laptop computer, a digital broadcasting terminal, personal digital assistants (PDA), a portable multimedia player (PMP), a navigation system and/or so on. FIGS. 1 to 4 are views illustrating an electronic device according to an embodiment of the present invention.

Figure 1:
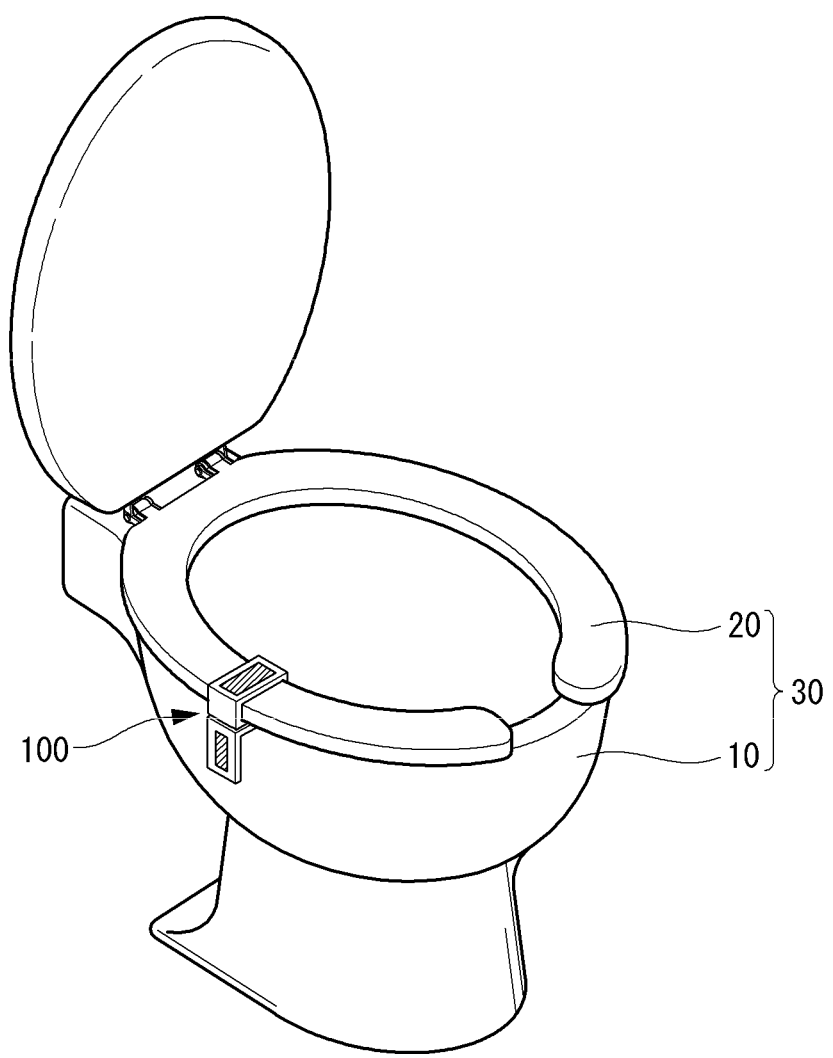
FIGS. 1 to 4 are views illustrating an electronic device according to an embodiment of the present invention.

Referring to FIG. 1, the electronic device 100 according to an embodiment of the present invention may be used while attached to a toilet 30.

The toilet 30 may be an instrument device that may dispose of urine and feces. At the time of the use of the toilet 30, the user may sit on the sitting-style toilet 30. At the time of the use of the toilet 30, the user's bio signals such as the user's heartbeat may be in a stable condition. That means that the user's emotion and/or body may enter into a stabilized condition at least for a few seconds when he uses the toilet 30. Accordingly, obtaining the user's bio signals at the time of using the toilet 30 might increase the possibility of obtaining reliable data regarding the user's health. According to an embodiment of the present invention, the electronic device 100 may obtain bio signals from the user upon use of the toilet 30 when the user's body and emotion remain in a stable condition.

As mentioned above, the toilet 30 may be a sitting-style toilet. For example, the toilet 30 may include a pottery bowl 10 and a seat cover 20 on the pottery bowl 10.

The pottery bowl 10 may have a structure for fulfilling the basic functions of the toilet 30. That means that it, by its structure, may retain water and runs the water to dispose of waste upon the user's operation.

The seat cover 20 may provide a structure by which the user may sit on the pottery bowl 10. The seat cover 20 has an opening in its middle enabling excreta to drop to the inside of the pottery bowl 10.

The electronic device 100 may be attached to a component of the toilet 30 such as the pottery bowl 10 and/or seat cover 20. The electronic device 100 may be located where the user, when using the toilet 30, may come in natural contact with at least a portion of the electronic device 100. For example, the electronic device 100 may be positioned where an upper side of the electronic device 100 may contact the user's thigh while the user sits on the toilet 30.

Figure 2:
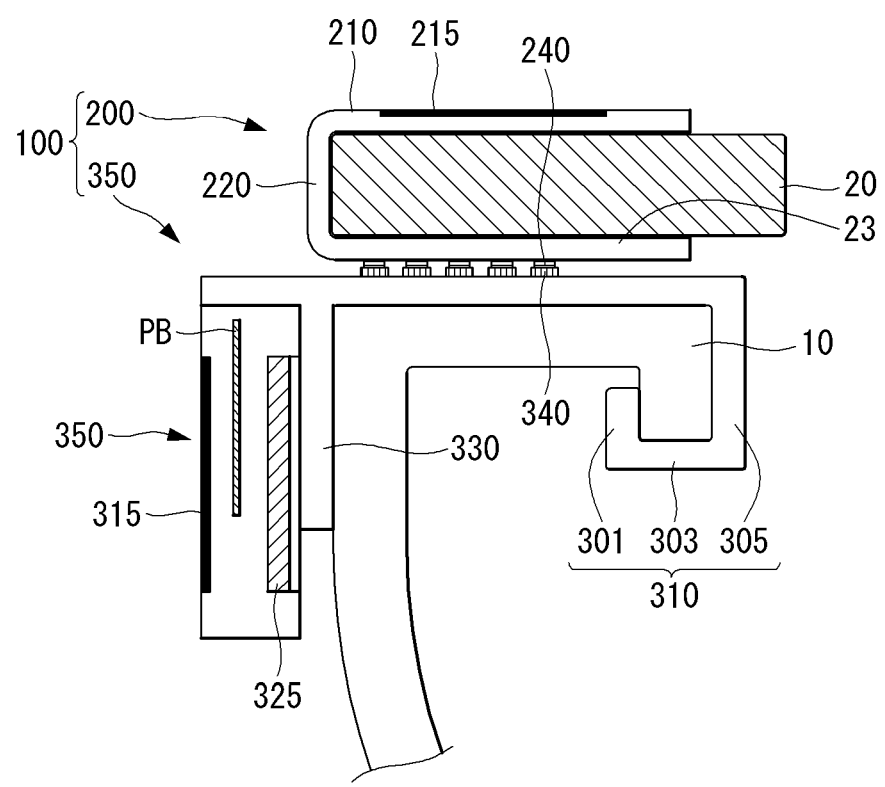

FIG. 2 is a cross-sectional view illustrating a coupling between the electronic device 100 and toilet 30 of FIG. 1.

As shown, the electronic device 100 may be in the form of being coupled with a plurality of structures constituting the toilet 30.

The electronic device 100 may include a cover assembly 200 and a bowl assembly 300.

The cover assembly 200 may be coupled with the seat cover 20. It may be coupled, contacting three surfaces of the seat cover 20. For example, a clip-shaped cover assembly 200 may be put in the seat cover 20.

The cover assembly 200 may include first to third surfaces 210, 220, and 230. The first surface 210 may be coupled to an upper side of the seat cover 20, the third surface 230 may be coupled to a lower side of the seat cover 20, and the second surface 220 may connect the first and second surfaces 210 and 230 with each other. A first electrode 215 may be positioned in the first surface 210, and a first terminal 240 may be positioned in the third surface 230.

The first electrode 215 may come in contact with the body of the user of the toilet 30. For example, the first electrode 215 may contact the user's thigh. While in use of the toilet 30, the user takes off at least a portion of the bottoms. Accordingly, when the user sits on the seat cover 20 to use the toilet 30, the first electrode 215 may be brought in contact with the user's thigh skin.

The first electrode 215 may apply a predetermined current and/or electrical signal to the user's thigh and/or may detect a current and/or electrical signal applied to other body portions of the user. Basic data by which the user's bio information may be computed may be obtained through the current and/or electrical signal applied and/or detected.

The first terminal 240 may function as a pathway connecting the cover assembly 200 to other structures of the electronic device 100. That means, for example, that the first terminal 240 may contact a second terminal 340 on the side of the bowl assembly 300. The cover assembly 200 and the bowl assembly 300 may transfer signals to each other by the contact between the first and second terminals 240 and 340.

The bowl assembly 300 may be left to be coupled with the pottery bowl 10. That means that the bowl assembly 300 may be positioned at a lower side of the seat cover 20. For instance, the bowl assembly may include an inner coupling part 310 coupled to a curved part inside the pottery bowl 10.

The inner coupling part 310 may be bent at one or more positions to surround the curved part and may include first to third portions 301, 303, and 305.

An extension 320 may be a portion extending from the inner coupling part 310 to the outside of the pottery bowl 10. The extension 320 may be a portion positioned at a lower side of the cover assembly 200. Over the extension 320 may be provided the second terminal 320 contacting the first terminal 240 of the cover assembly 200. An outer coupling part 330 may be provided at a side of the extension 320.

The outer coupling part 330 may be shaped to extend from the extension 320 to the pottery bowl 10 and to come in tight contact with the pottery bowl 10. The outer coupling part 330 and the inner coupling part 310 allow the pottery bowl 300 to be securely attached to the pottery bowl 10. A body 350 may be coupled to a side of the outer coupling part 330.

The body 350 may be positioned at an outside of the bowl assembly 300. That means that the body 350 may be located outside the pottery bowl 10. The body 350 placed outside the pottery bowl 10 may correspond to the position where contacts a hand of the user using the toilet 30. That means that the body 350 may be provided at the position where the user's hand is naturally positioned when he puts his arm down while seated on the toilet 30. The body 350 may include various components necessary for the operation of the electronic device 100. As an example, the body 350 may include the second electrode 315, a PCB (PB), and a battery 325.

The second electrode 315 may be exposed to an outside surface of the body 350. That means that the second electrode 315 may be positioned where a hand of the user is naturally brought in contact while in use of the toilet 30. The second electrode 315 may apply a predetermined current and/or electrical signal to the user's body it contacts and/or may detect a current and/or electrical signal applied to other body portions of the user.

The second electrode 315 may perform a certain function in pair with the first electrode 215. That means, for example, that the electronic device 100 may be operated based on a value sensed by the first electrode 215 from a current and/or electrical signal applied from the second electrode 315 and passing through the user's body. Data obtained through the current and/or electrical signal applied and/or detected through the first and second electrodes 315 and 215 may be used to estimate/compute the user's body composition analysis, muscle fat analysis, obesity diagnosis, lean balance, edema, visceral fat area, body shape domain, growth chart, weight control, basal metabolic rate, fitness score, and body composition history.

The second electrode 315 may contact the user's body terminal. For example, as set forth above, the second electrode 315 may be positioned where a finger of the user seated on the toilet 30 forms a natural contact. Accordingly, the user's bio signal may be more correctly measured through the current and/or control signal sensed through the second electrode 315 and/or applied to the second electrode 315.

The PCB (PB) may be positioned inside the body 350. The PCB (PB) may generate control signals necessary for the operation of the electronic device 100.

The battery 325 may supply power necessary for the operation of the electronic device 100.

Figure 3:
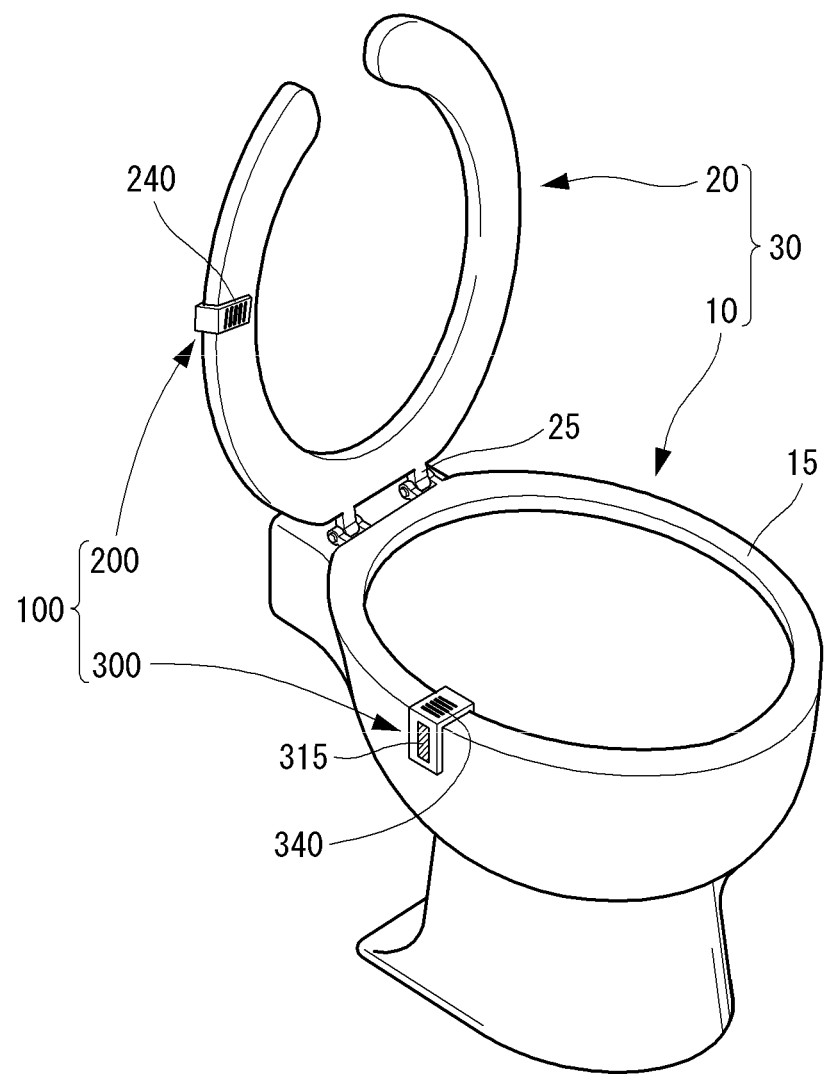

FIG. 3 illustrates an example in which the seat cover 20 is in a changed position. As shown in FIG. 3, the seat cover 20 may be in a position pivoted about a hinge 25. That means that a position change may arise from a first position as shown in FIG. 1, where the seat cover 20 and the pottery bowl 10 are mutually in tight contact to a second position as shown in FIG. 3, where the seat cover 20 remains separated from the pottery bowl 10.

When the position of the seat cover 20 changes, the cover assembly 200 and the bowl assembly 300 may be spaced apart from each other. In the electronic device 100 according to an embodiment of the present invention, the seat cover 20 may be readily opened and closed, with the cover assembly 200 coupled with the seat cover 20, enabling easy cleaning of the toilet 30.

Figure 4:
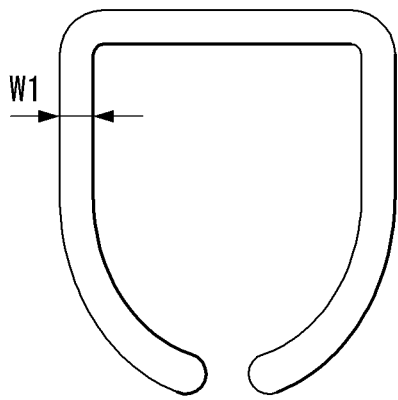
Figure 4:
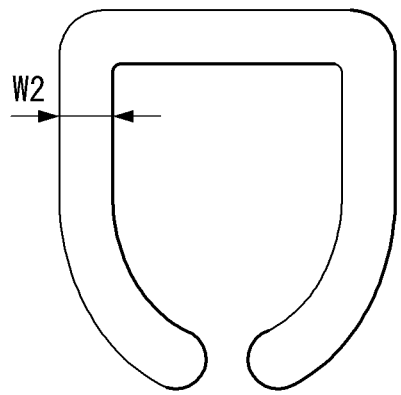
Figure 4:
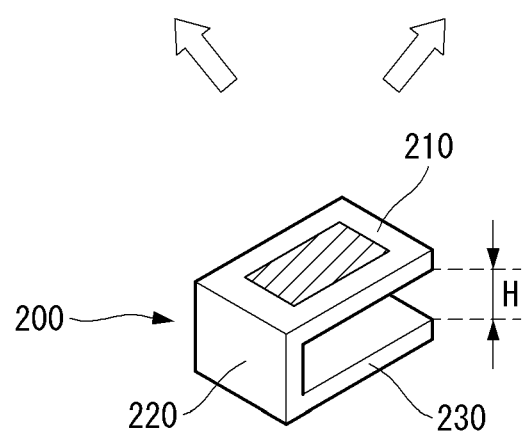

As shown in FIG. 4, the electronic device 100 according to an embodiment of the present invention may be effectively used in various types of seat covers 20. For example, the seat cover 20 may come in type A and type B. That means that the seat cover 20 may have a width W1 or W2.

According to an embodiment of the present invention, the cover assembly 200 may slide in and out from a side surface of the seat cover 20 to couple with the seat cover 20. Accordingly, it may be used for a diversity of seat covers 20.

A height between the first surface 210 and third surface 230 of the cover assembly 200 may be H. The height H of the cover assembly 200 formed of rubber or plastic may experience an elastic deformation depending on the shape and/or size of the seat cover 20. This enables the use in various sizes of seat cover 20.

Figure 5:
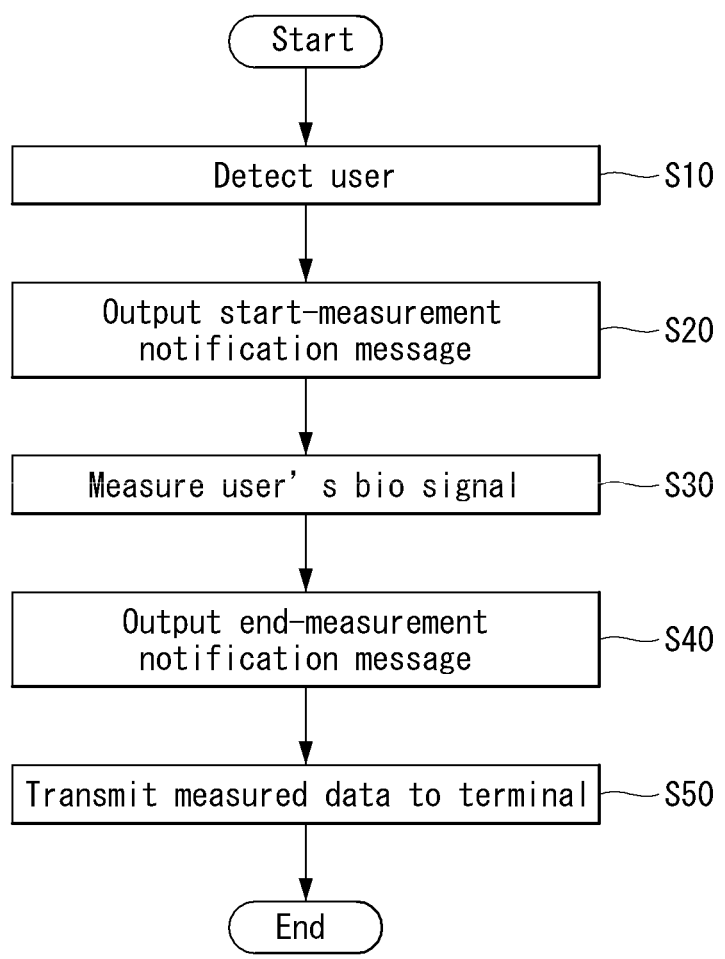
FIG. 5 is a flowchart illustrating an operation of an electronic device according to an embodiment of the present invention.

FIG. 5 is a flowchart illustrating an operation of an electronic device according to an embodiment of the present invention.

As illustrated in FIG. 5, according to an embodiment of the present invention, a controller 180 of the electronic device 100 may perform the step S10 of sensing a user.

The toilet 30 equipped with the electronic device 100 may be shared by multiple users. For example, that means that the same toilet 30, when installed in a home, may be shared by the family members. The electronic device 100 may sense which one of a plurality of users is in use of the toilet 30.

Such sensing may be performed based on per-user features. For example, that means that a particular user may be distinguished from other users based on, e.g., the users' weights or manners they sit on the seat cover 20, which differ from user to user, and/or results of sensing the current and/or control signal. Such sensing may be performed based on the user's terminal. For example, in the case where the terminal approaches within a predetermined distance of the electronic device 100 and the user then uses the toilet 30, the user of the terminal may be determined to use the toilet 30. The user's terminal approaching may be sensed through a connection of a B/T signal and/or NFC tagging.

The step S20 of outputting a start-measurement notification message may proceed.

When the user seats on the seat cover 30, the measurement may begin. The controller 180 may notify, through a message including a sound and/or color output, that the user's state is to be measured.

The controller 180 may output a message instructing the user to perform an operation necessary for measurement. For example, upon sensing the user sitting on the seat cover 20, a message may be output to instruct to bring his hand in contact with the second electrode of the electronic device. When the user brings his hand in contact at a right position, a message may be output to indicate that measurement starts.

The step S30 of measuring the user's bio signal may be carried out.

The user's bio signal may be measured through exchange of currents and/or control signals between the first and second electrodes 215 and 315 as described above. At least one of the first and second electrodes 215 and 315 may output a current and/or control signal at least once. The output current and/or control signal may be deformed while passing through the user's body. At least one of the first and second electrodes 215 and 315 may sense the current and/or control signal deformed while passing through the user's body. The controller 180 may measure and/or compute the user's bio signal based on the current and/or control signal sensed.

The step S40 of outputting an end-measurement notification message may proceed.

The step S50 of transmitting the measured data to the terminal may proceed. The controller 180 may send the measured data to another terminal. The other terminal may be a mobile terminal of the user measured and/or a particular external server.

FIGS. 6 to 11 are views illustrating the operation of the electronic device shown in FIG. 5.

As shown in FIGS. 6 to 11, according to an embodiment of the present invention, the electronic device 100 may measure the user's bio information and transfer the measured bio information to a terminal.

Figure 6:
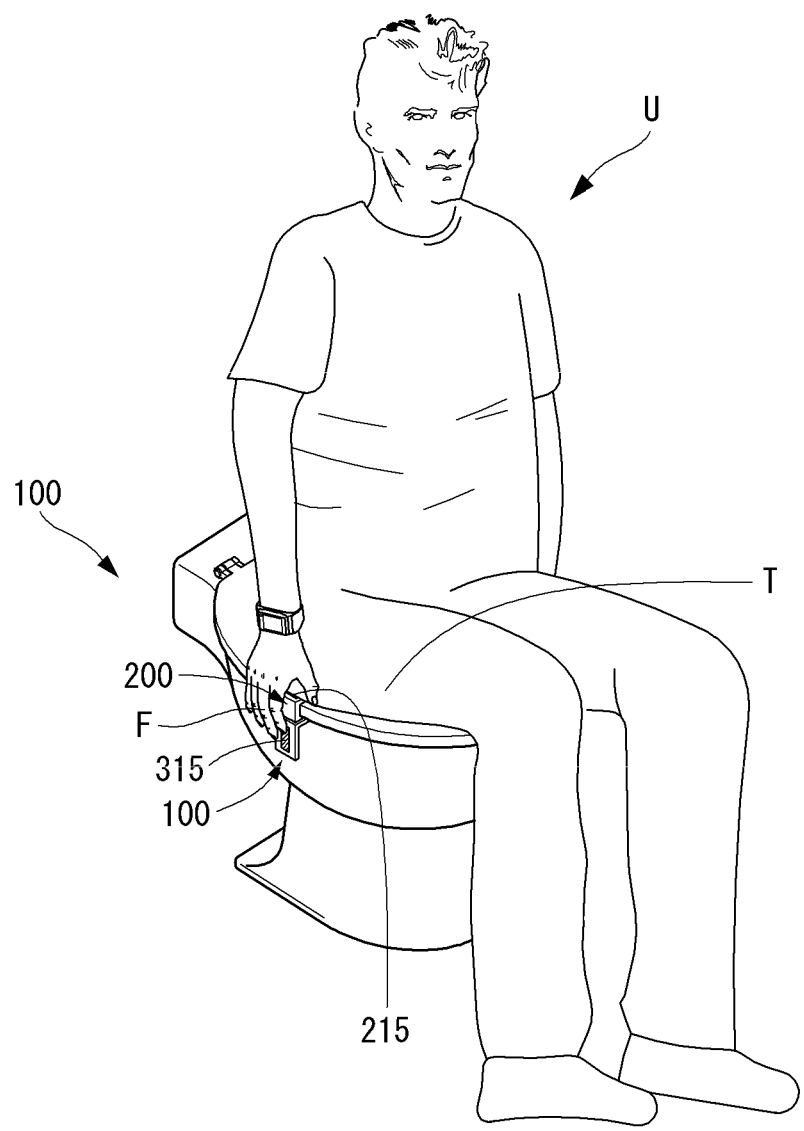
FIGS. 6 to 11 are views illustrating the operation of the electronic device shown in FIG. 5.
Figure 7:
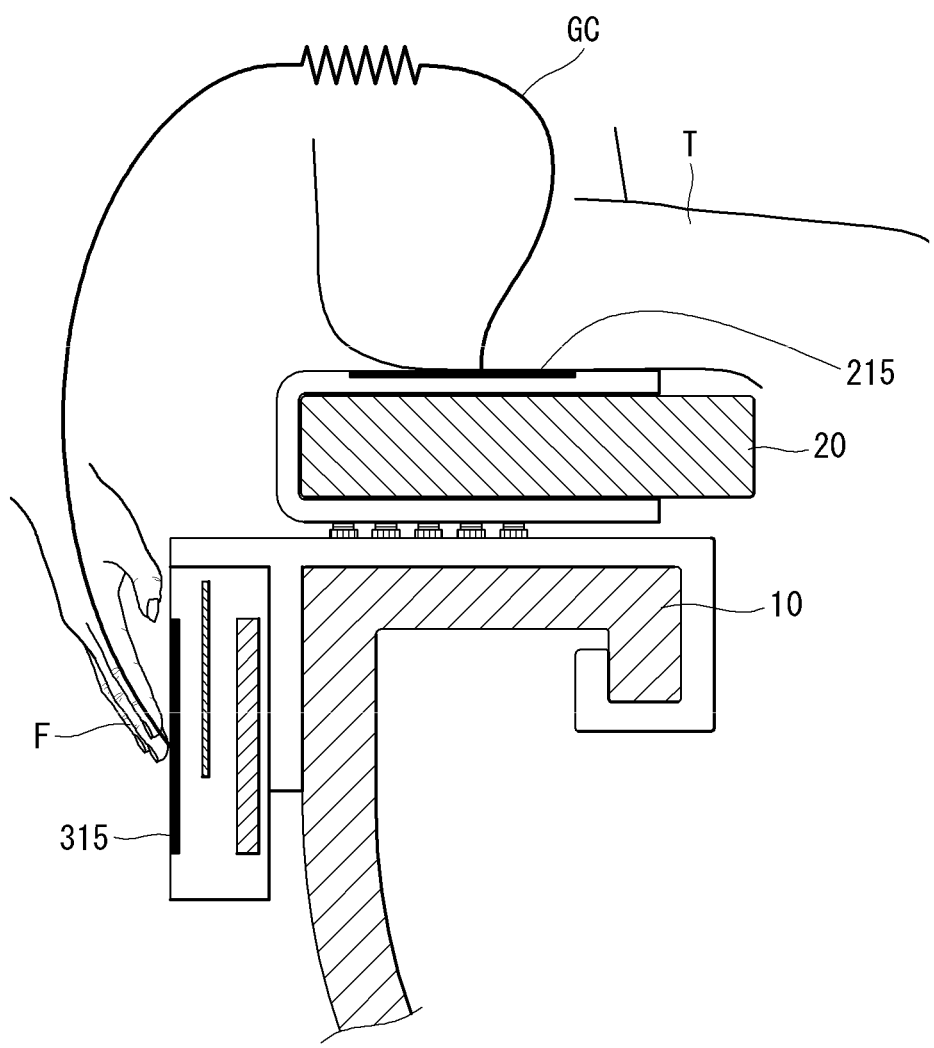

As shown in FIGS. 6 and 7, the electronic device 100 may remain attached to the toilet 20. The electronic device 100 may obtain bio information of the user using the toilet 20.

A thigh T of the user U may contact the first electrode 215. A finger F of the user U may contact the second electrode 315. When the respective body portions of the user U contact the first and second electrodes 215 and 315, an electrical path GC may be formed passing through the user's body.

The electrical path GC passing through the user's body may show voltages and resistances varying depending on the user's body conditions. That means, for example, that different voltages and resistances may be shown when passing through fat and muscle, respectively.

The controller 180 may compute the user's bio information based on a variation in the current sensed by at least one of the first and second electrodes 215 and 315 while a current applied from the other of the first and second electrodes 215 and 315 passes through the electrical path (GC).

The first and second electrodes 215 and 315 may contact the user's thigh T and finger F as described above. That means that the electrical path (GC) may be formed between an end of the user's arm and the user's leg.

Figure 8:
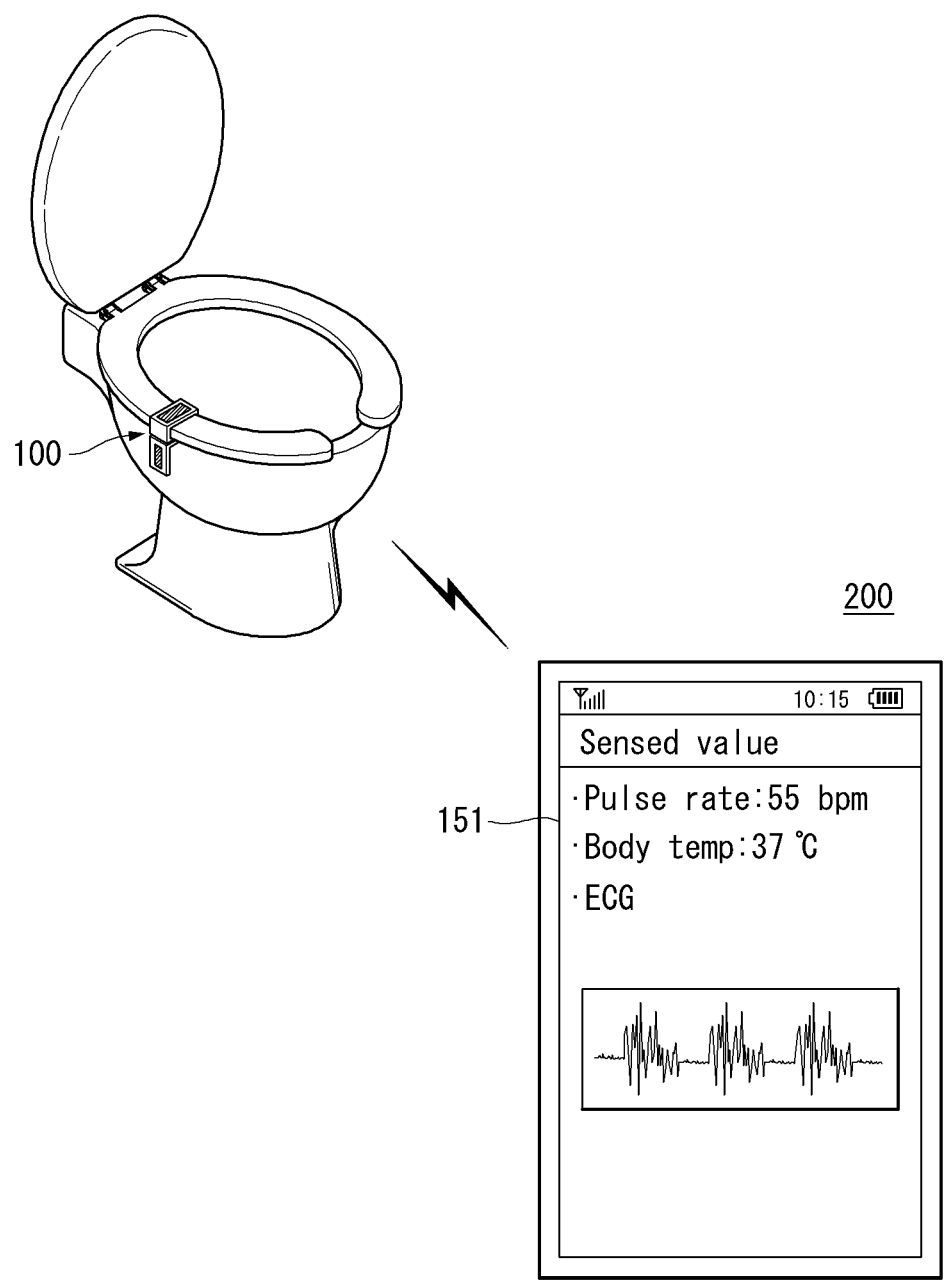
Figure 9:
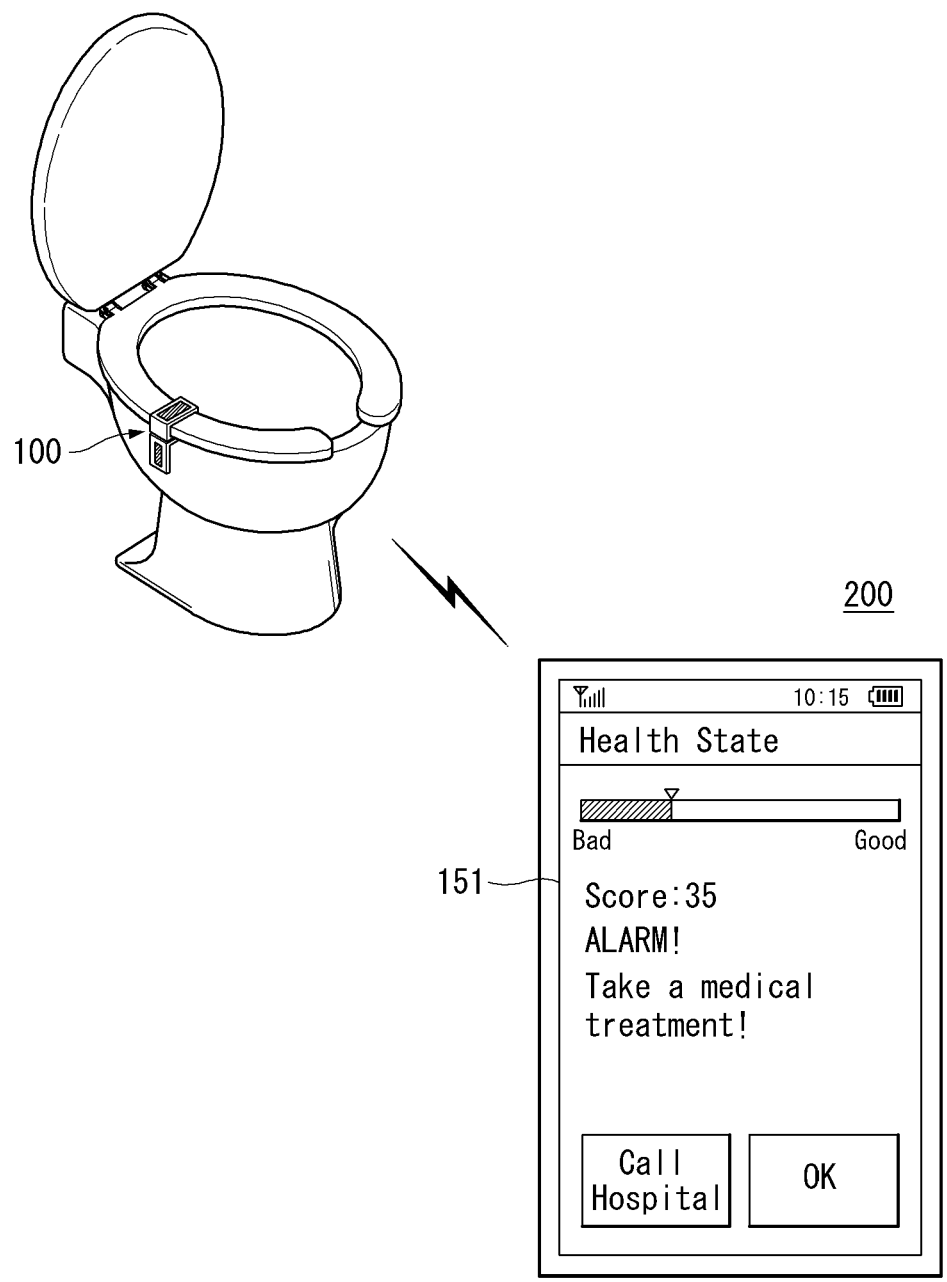
Figure 10:
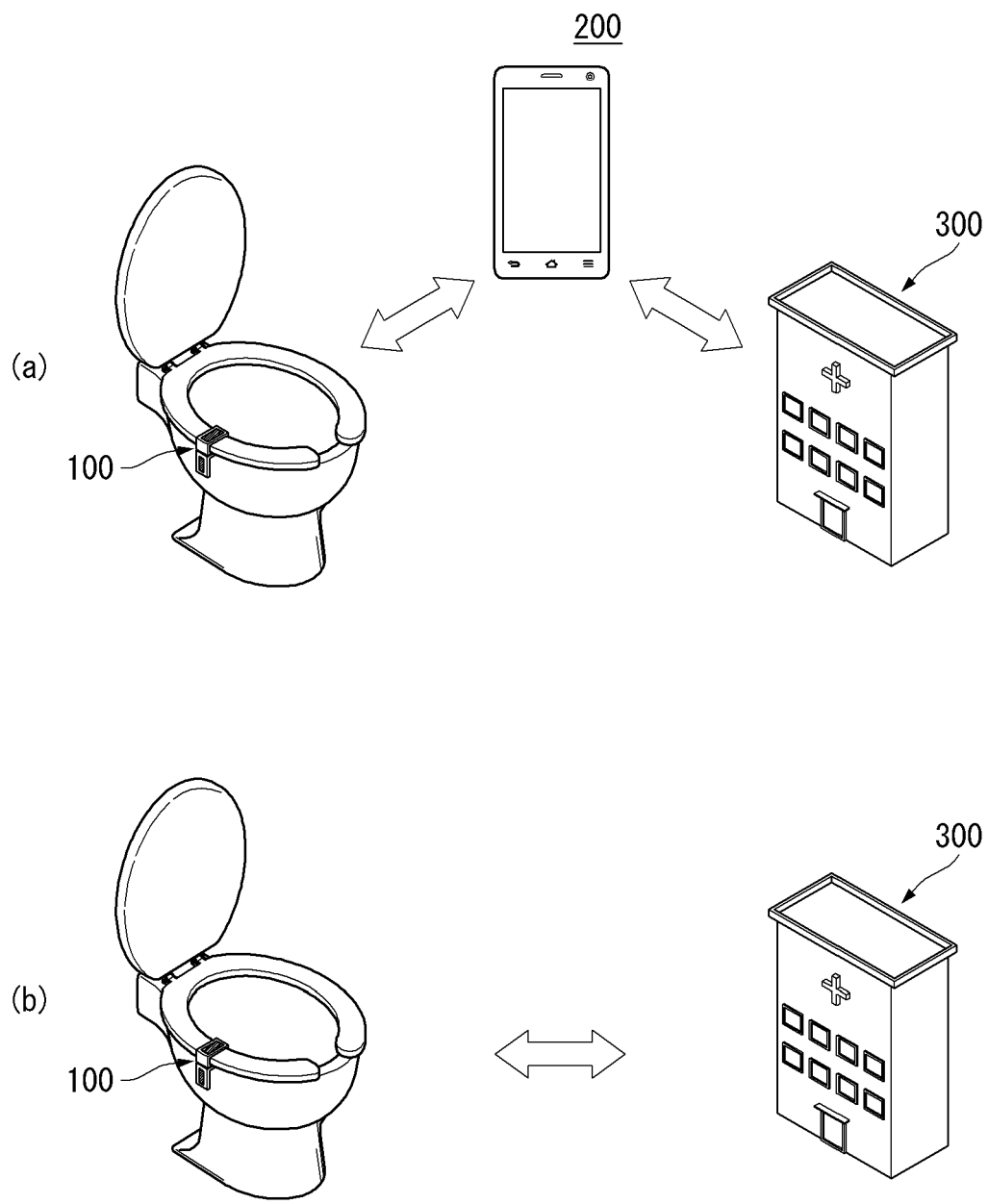

FIGS. 8 to 10 illustrate the use of the user's bio information obtained.

As shown in the figures, according to an embodiment of the present invention, the electronic device 100 may transmit the user's bio information obtained to another terminal 200. The other terminal 200 may be a mobile terminal carried by the user.

As shown in FIG. 8, raw data obtained from the electronic device 100 may be transmitted to the other terminal 200. For example, data such as the user's heartbeat, body temperature, and ECG may be transmitted. The other terminal 200 may store and/or display the raw data received.

As shown in FIG. 9, the other terminal 200 may process the obtained information. For example, that means that healthcare information may be generated. The healthcare information may include an index regarding the user's health condition. The user may prefer an index from which the user's health condition may be easily recognized to various types of bio information data that is difficult to appreciate.

A display unit 151 of the other terminal 200 may display a call button BC. For example, that means that a button may be displayed which enables a call connection with a hospital or other special organizations from which the user may get relevant treatments and/or advice when the user's health condition is under a reference value or less.

As shown in FIG. 10(a), the information obtained from the electronic device 100 and transferred to the other terminal 200 may be re-transmitted to an external organization 300. For example, the information may be transmitted to a server of the external organization 300.

The user's bio information may be sent to the external organization 300 and managed by the external organization 300. According to an embodiment of the present invention, the electronic device 100 may obtain the user's bio information at the time of using the toilet 20. That means that no separate process for measuring the bio information may be required to enable more data to be obtained. Based on the same, the user's health may be thus managed more effectively.

As illustrated in FIG. 10(b), the electronic device 100 may directly send the obtained information to the external organization 300.

The electronic device 100 may selectively conduct such transmission to the external organization 300. That means, for example, that the transmission may be made to the other terminal 200 when the user's health condition measured is under a normal situation, and to the external organization 300 when the user's health condition is at emergency. Accordingly, a relevant step may be taken more quickly.

Figure 11:
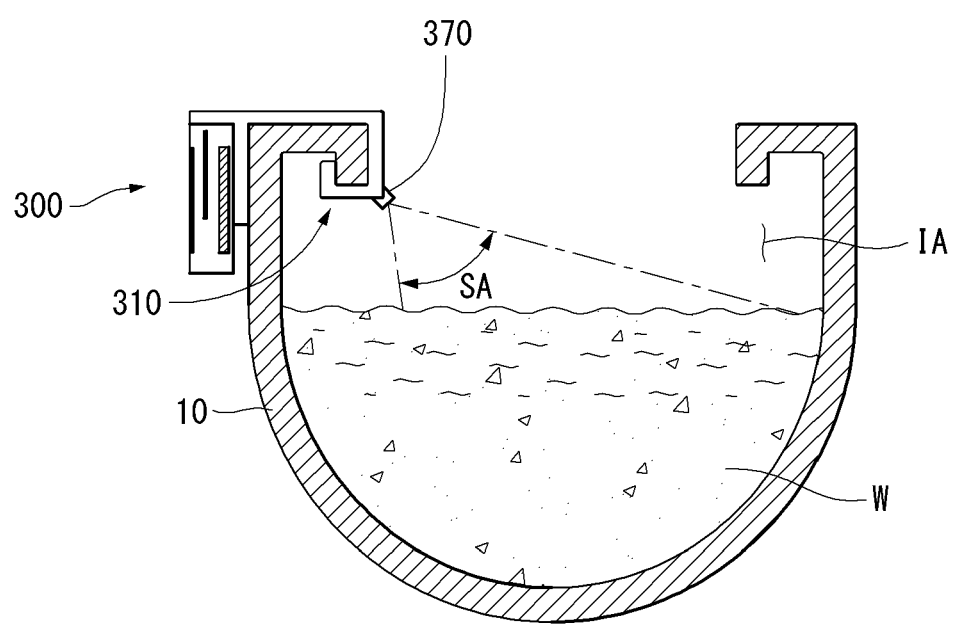

As shown in FIG. 11, according to an embodiment of the present invention, the electronic device 100 may directly observe the user's excreta. For example, an observation sensor 370 may be provided inside the bowl assembly 300.

The observation sensor 370 may be a camera sensing images. The observation sensor 370 may observe the inside of the pottery bowl 10. That is, the cleaning water W contained in the pottery bowl 10 may be observed within a predetermined observation range SA. Thus, the shape and/or color or other states of the user's feces and/or urine may be sensed through the observation sensor 370. The states sensed may be utilized as reference material to evaluate the user's health condition.

Figure 12:
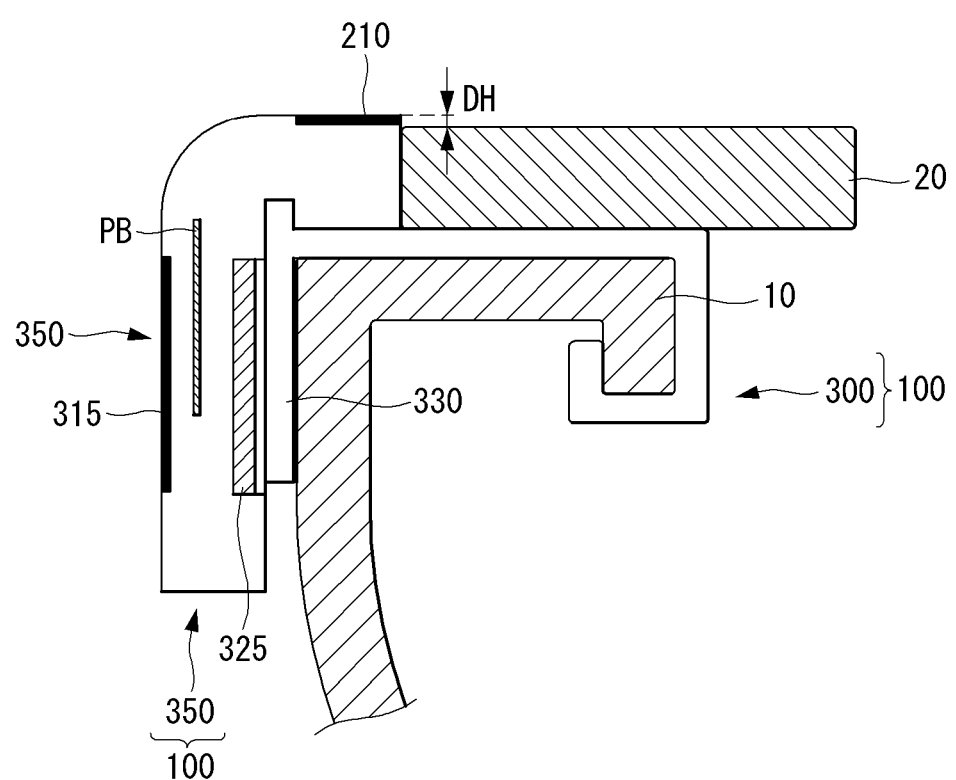
FIGS. 12 to 14 are views illustrating an electronic devices according to another embodiment of the present invention.
Figure 13:
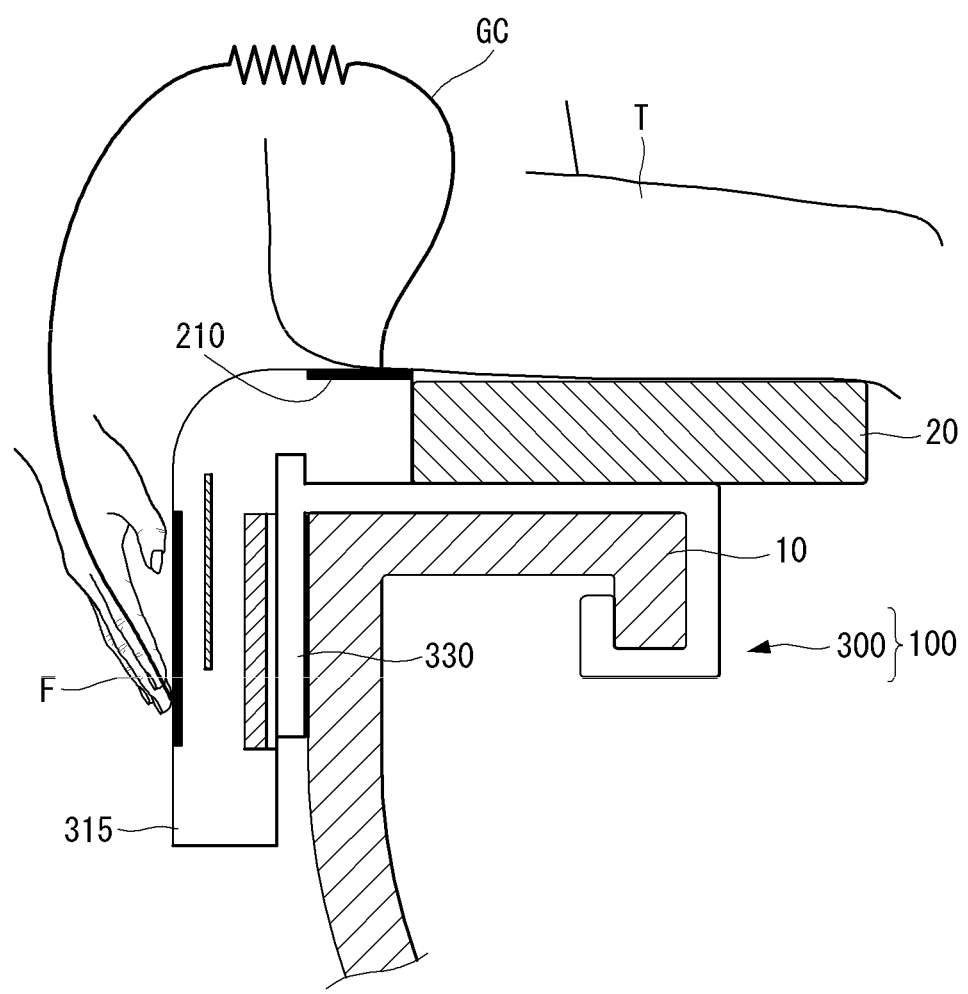
Figure 14:
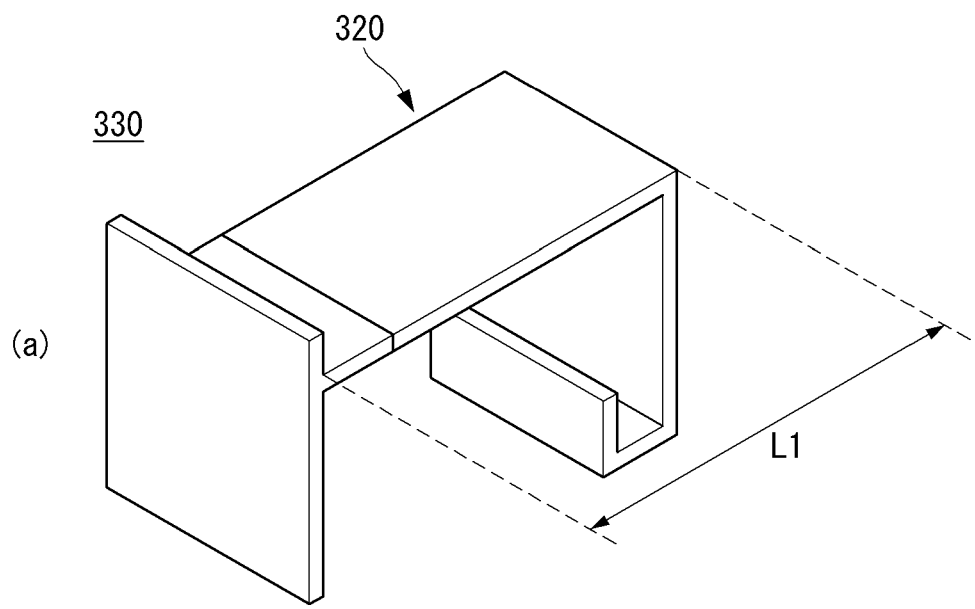
Figure 14:
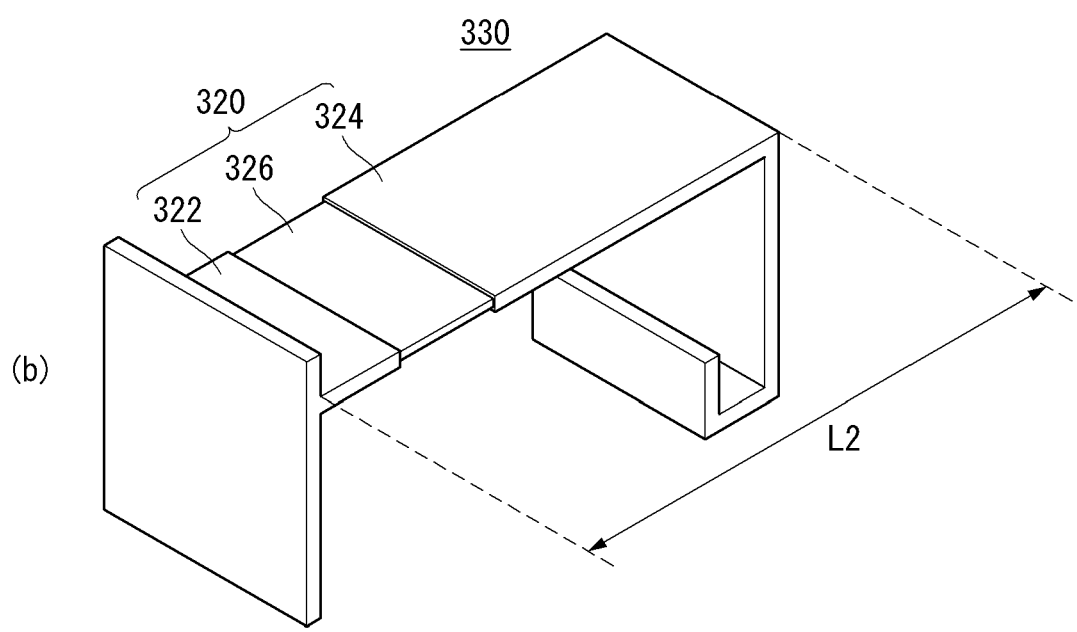

FIGS. 12 to 14 are views illustrating an electronic devices according to another embodiment of the present invention.

As shown in the figures, according to an embodiment of the present invention, the bowl assembly 300 of the electronic device 100 may be coupled with the pottery bowl 10 without direct connection between the components of the electronic device 100 and the seat cover 20. Since the components of the electronic device 100 are not coupled with the seat cover 20, the seat cover 20 may be used more freely. Further, even without considering various shapes of the seat cover 20, the primary cell may be designed.

As shown in FIG. 12, the body 350 may be left to couple with an outer side of the bowl assembly 300. The first electrode 215 may be positioned at an upper side of the body 350, and the second electrode 315 may be positioned in a side surface of the body 350. Inside the body 350 may be provided components necessary for the operation of the electronic device 100.

The first electrode 215 may project upwards by DH beyond the seat cover 20. Accordingly, the user's body, e.g., thigh, may make a natural contact with the first electrode 215.

As shown in FIG. 13, the thigh T of the user using the toilet 30 may contact the first electrode 215, and the finger F may contact the second electrode 315. For natural contact to the thigh T, the first electrode 215 may be provided at a position leaning from an upper side of the body 350 to the seat cover 20.

As shown in FIG. 14, the beacon frame 330 may be changed in its form to correspond to the size and/or shape of the toilet.

As shown in FIG. 14(a), the extension 320 of the bowl assembly 330 may have a first length L1.

As shown in FIG. 14(b), the extension 320 may be changed in length to have a second length L2. That means, for example, that in the case where the pottery bowl 10 has a larger width, the extension 320 of the pottery bowl 10 may be varied to have the second length L2 upon use. The extension 320 may include first to third upper plates 322, 324, and 326. The second upper plate 324 may slidingly couple to the first and third upper plates 322 and 326. That means that it is positioned inside at least one of the first and third upper plates 322 and 326 and may be slid by the user's manipulation to be exposed to the outside. FIGS. 15 to 21 are views illustrating an electronic devices according to another embodiment of the present invention.

Figure 15:
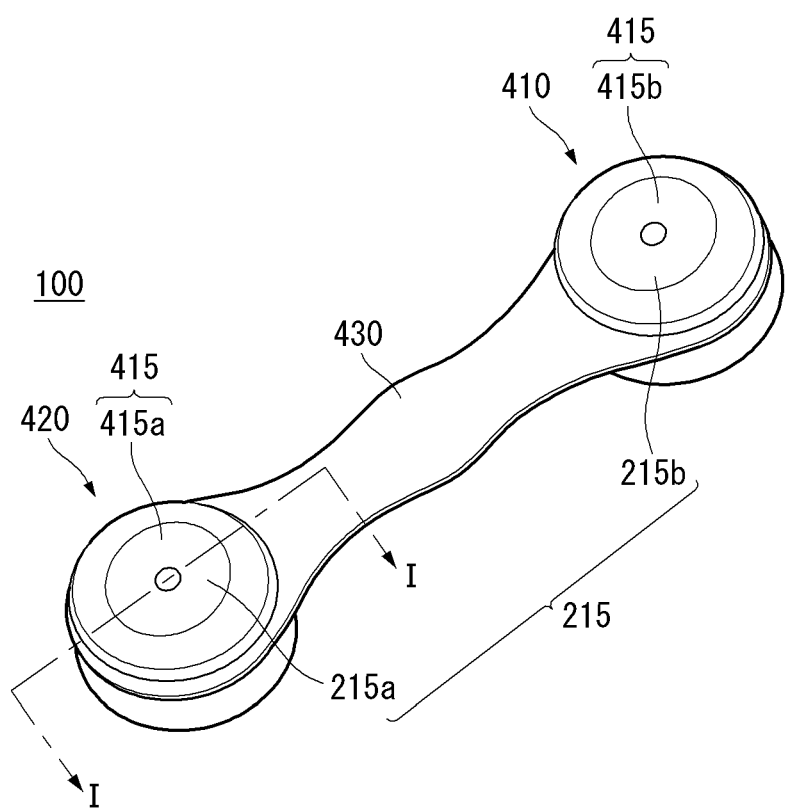
FIGS. 15 to 21 are views illustrating an electronic devices according to another embodiment of the present invention.

As shown in the figures, according to this embodiment of the present invention, the electronic device 100 may be in the form of being not attached to the toilet. As shown in FIG. 15, according to the instant embodiment of the present invention, the electronic device may include first and second bodies 410 and 420 and a third body 430 connecting the first and second bodies 410 and 420 with each other.

The first and second bodies 410 and 420 each may be shaped as a cylinder. The first and second bodies 410 and 420 may correspond to the size and/or shape of the user's knee or hand. The user may bring the first and second bodies 410 and 420 in contact with his right and left knees, respectively, while grabbing the second image processing module 420 with his right and left hands, respectively, to thereby measure bio information.

A first electrode 415 may be positioned in an upper side surface of the first and second bodies 410 and 430. The first electrode 415 over the first and second bodies 410 and 430 may correspond to the user's hands taking hold of the first and second bodies 410 and 430. That means that when the user grabs the first and second bodies 410 and 430, his fingers and/or palm may be brought in tight contact with the first electrode 415.

Figure 16:
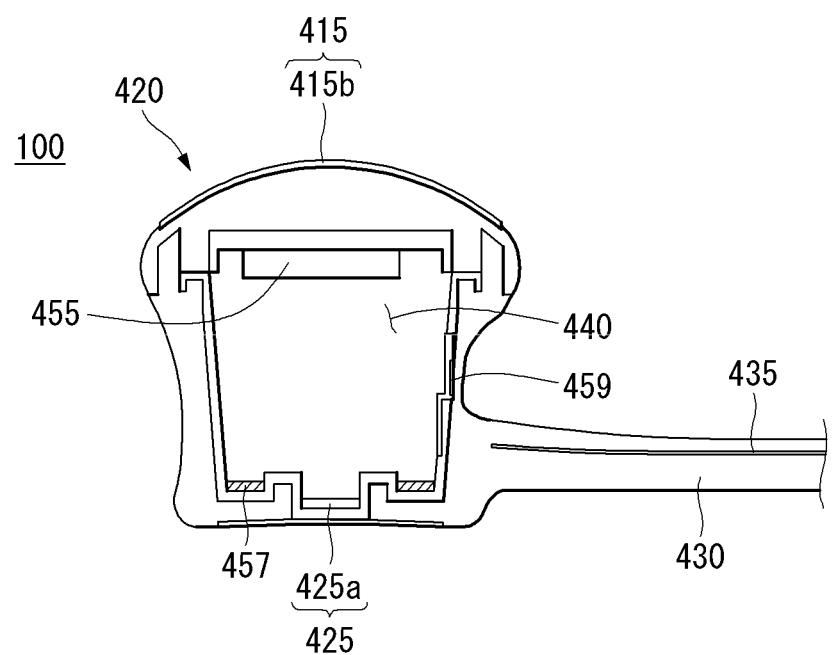

FIG. 16 illustrates the second body 420. Unless specially stated otherwise, the first body 410 might not have the same component as the second body 420. Over the second body 420 may be provided the first electrode 415.

A battery 455 may be provided inside the second body 420. The battery 455 may be present only in one of the first and second bodies 410 and 420. That means, for example, that the battery 455 may be positioned in the second body 420 only, and that the first body 410 may also be operated by the battery 455 in the second body 420.

A cavity 440 may be formed inside the second body 420. That means that the second body 420 may be empty inside. The internal cavity 440 may serve as a soundbox for a speaker (not shown) provided in the electronic device 100. Or, as described in the relevant parts, it may be a space for coupling the first and second bodies 410 and 420 with each other.

The second electrode 425 may be provided at a lower side of the second body 420. The second electrode 425 may be shaped as a ring along a lower surface of the circular second body 420. The ring-shaped second electrode 425 may easily come in tight contact with the user's knee.

A temperature sensor 457 may be provided at a lower side of the second body 420. The temperature sensor 457 may measure the temperature of the user's body tightly contacting the second body 420.

The second body 420 may be covered on its outer side with an outer coat 435 formed of rubber.

The outer coat 435 may form a single body with the third body 430 connecting the first and second bodies 410 and 420 with each other. That means that the third body 430 may also be formed of rubber. Accordingly, the third body 430 may be freely bent.

An FPCB 435 may be provided inside the third body 430. The FPCB 435 may electrically connect the first and second bodies 410 and 420 with each other to convey necessary signals therebetween.

Figure 17:
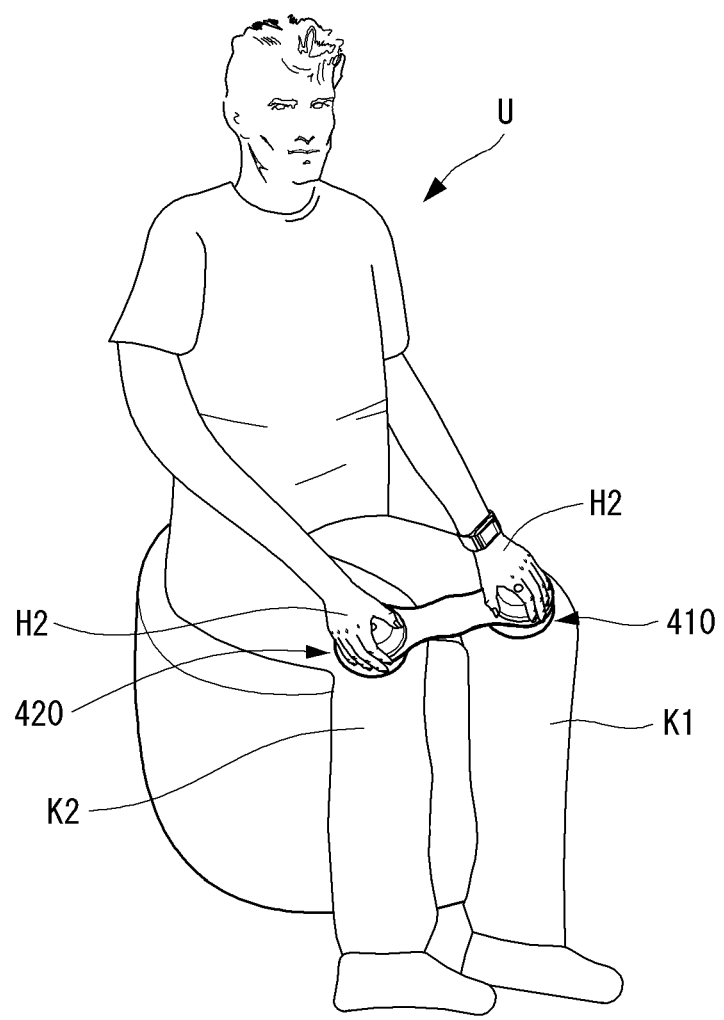

As shown in FIG. 17, the user U may make use of the electronic device 100 while in use of the toilet. That means that the user may grab the first and second bodies 410 and 420 of the electronic device 100 with his hands H1 and H2 and placing the same on his knees K1 and K2 while seated on the toilet, thereby measuring bio signals.

Figure 18:
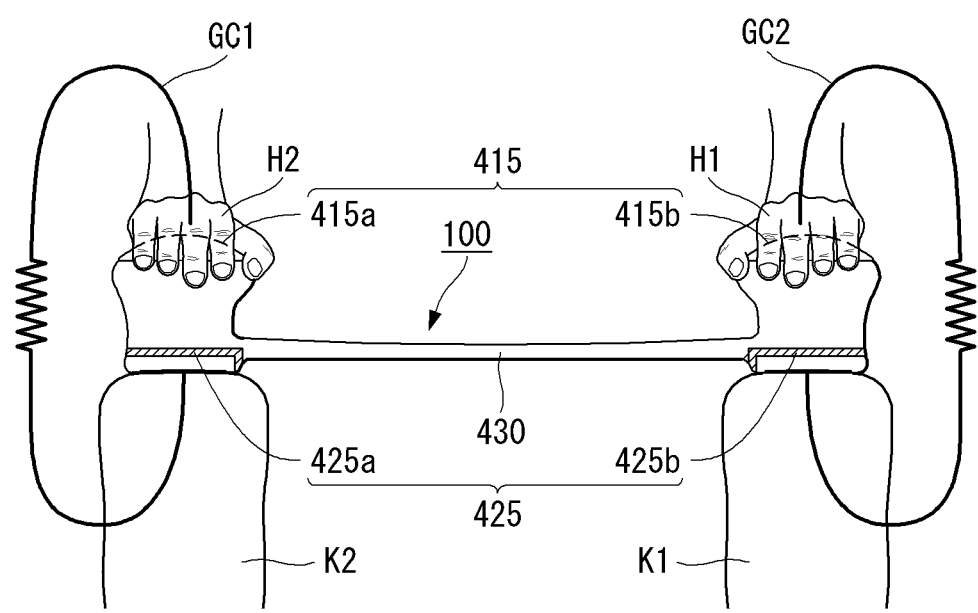
Figure 19:
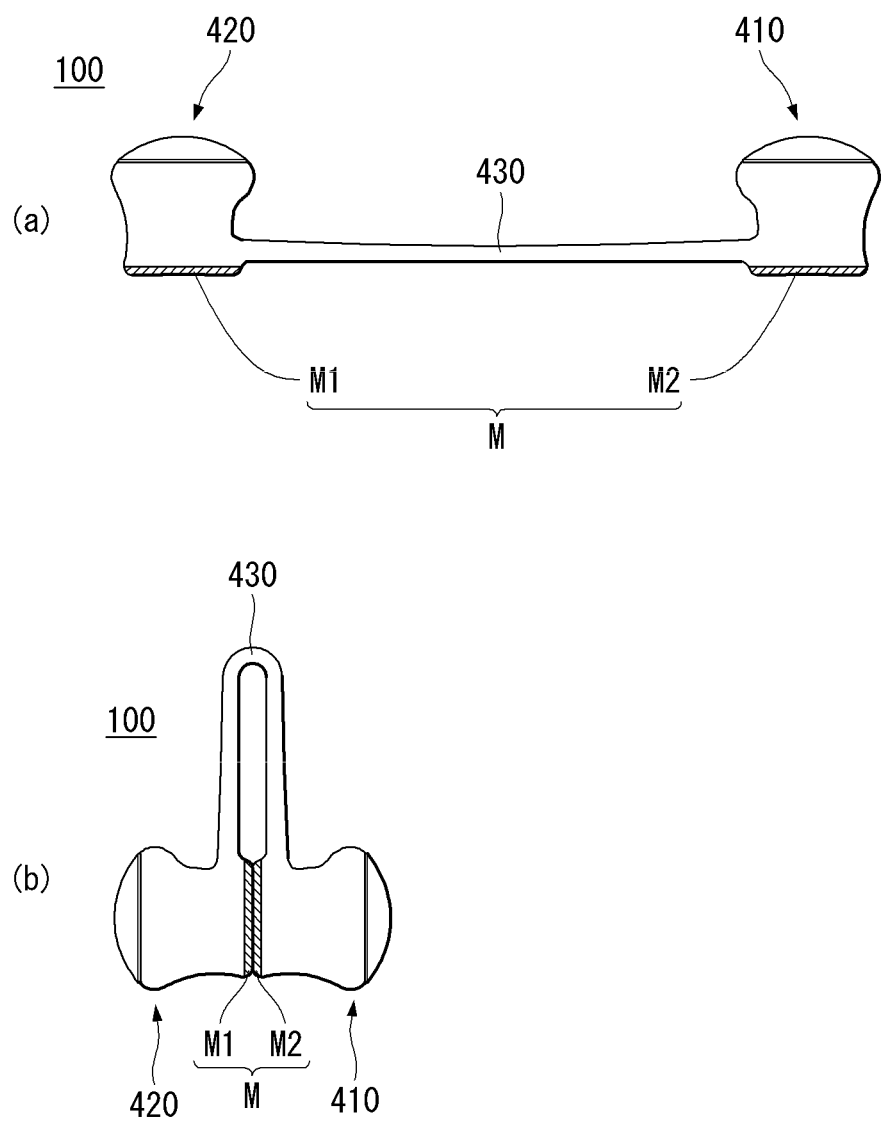
Figure 20:
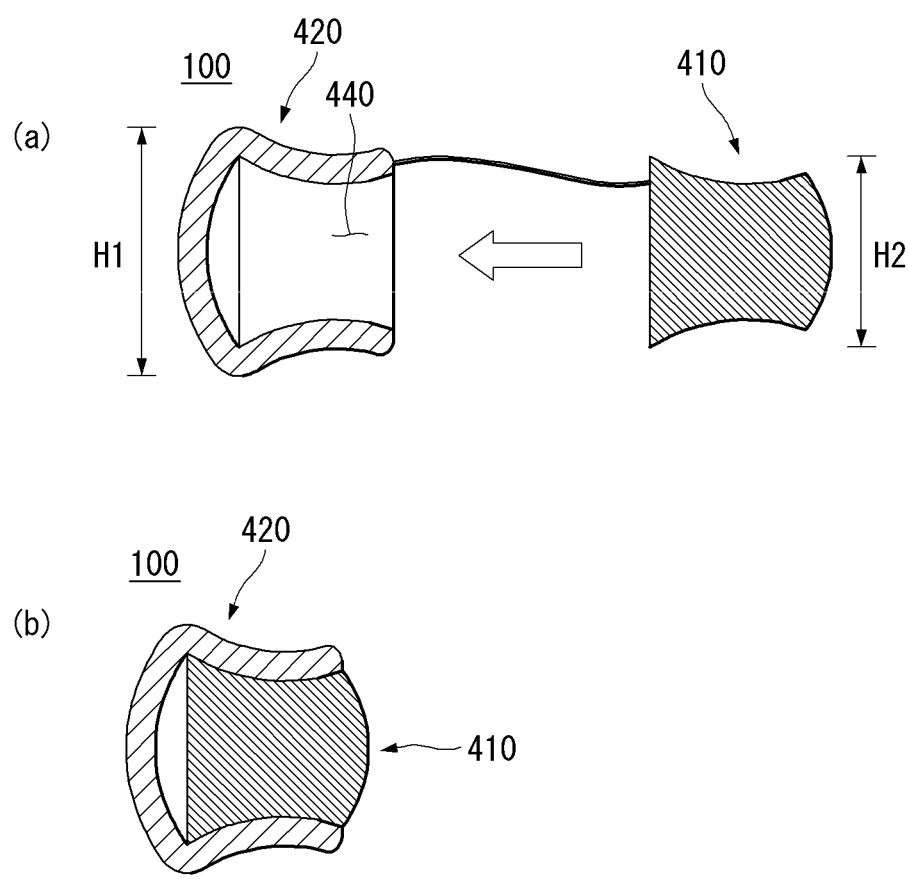
Figure 21:
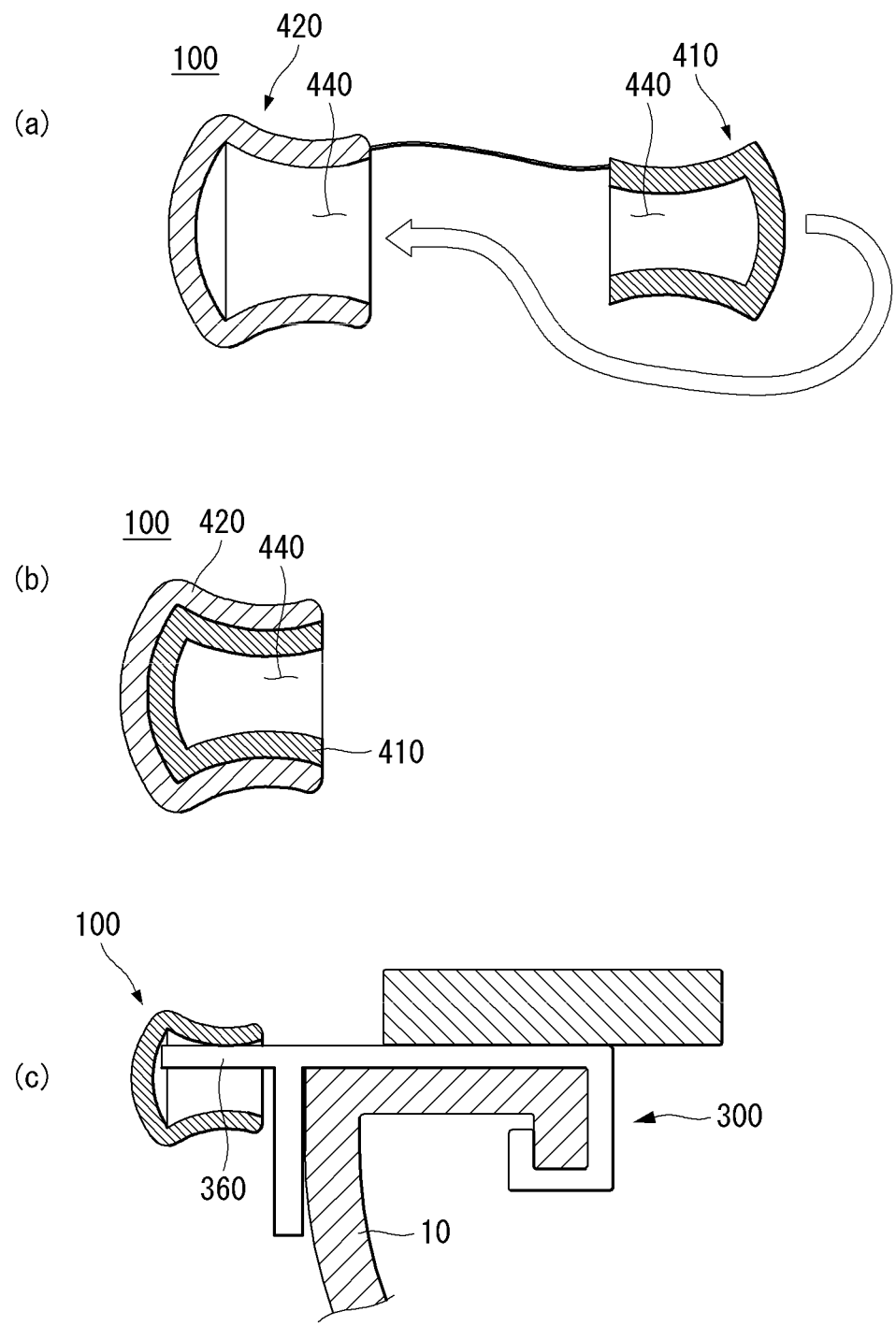

As shown in FIG. 18, first and second electrical paths GC1 and GC2, respectively, may be formed between the user's hand H1 and knee K1 and between the user's hand H2 and knee K2. The first and second electrical paths GC1 and GC2 may be formed to have other various forms than those shown. For example, an electrical path may also be established between the first hand H1 and the second knee K2.

As shown in FIG. 19(a), magnets M may be positioned on the first and second bodies 410 and 420. That means, for example, that first and second magnets M1 and M2 may be positioned in the bottoms of the first and second bodies 410 and 420, respectively. The first and second magnets M1 and M2 may have opposite polarities.

The first and second magnets M1 and M2 in the first and second bodies 410 and 420 may be not in contact with each other, which is referred to as a first state. In the first state, the electronic device 100 may be in the condition of being available for measurement of bio signals.

As shown in FIG. 19(b), when the first and second bodies 410 and 420 come closer to each other, they may be attracted to each other by the first and second magnets M1 and M2. The first and second bodies 410 and 420 tightly attached to each other might not be separated from each other until before an external force larger than the magnetic force of the magnets M is exerted.

When the first and second bodies 410 and 420 are tightly attached to each other by the magnets M may be referred to as a second state. The second state may be under the situation where the electronic device 100 is not in use. In the second state, the electronic device 100 may be hung at a certain position using the third body 430.

The controller 180, when turning into the second state, may deactivate at least one function of the electronic device 100. For example, the function of measuring bio signals may be deactivated.

As shown in FIG. 20(a), the first body 410 may have a height H2, and the second body 420 may have a height H1. The second body 420 may have a cavity 440 inside, which is sized to receive the first body 410.

As shown in FIG. 20(b), the first body 410 may be inserted into the inside of the second body 420. When the first and second bodies 410 and 420 are folded to a single piece, the electronic device 100 may be easily reserved. While folded, at least one of the first and second bodies 410 and 420 may be elastically deformed.

When the first and second bodies 410 and 420 are folded, the controller 180 may deactivate at least one function of the electronic device 100. For example, the function of measuring bio signals may be deactivated. Even when the function of measuring bio signals are deactivated, a function for transmitting measured data may be activated. That means that some functions may be deactivated while other functions may be activated.

As shown in FIGS. 21(a) and (b), an upper side surface of the first body 410 may be inserted to the second body 420. As the upper side surface of the first body 410 is inserted into the second body 420 and the first and second bodies 410 and 420 are thus joined together, an opening may be formed at a side of the cavity 440.

As shown in FIG. 21(c), the electronic device 100 having the first and second bodies 410 and 420 joined together may be coupled to the bowl assembly 300 fitting over the pottery bowl 10. That means that the bowl assembly 300 may combine into the opening formed at a side of the first and second bodies 410 and 420. As the electronic device 100 may be received in the pottery bowl 10, the user may make more convenient use of the electronic device 100 when in use of the toilet.

Figure 22:
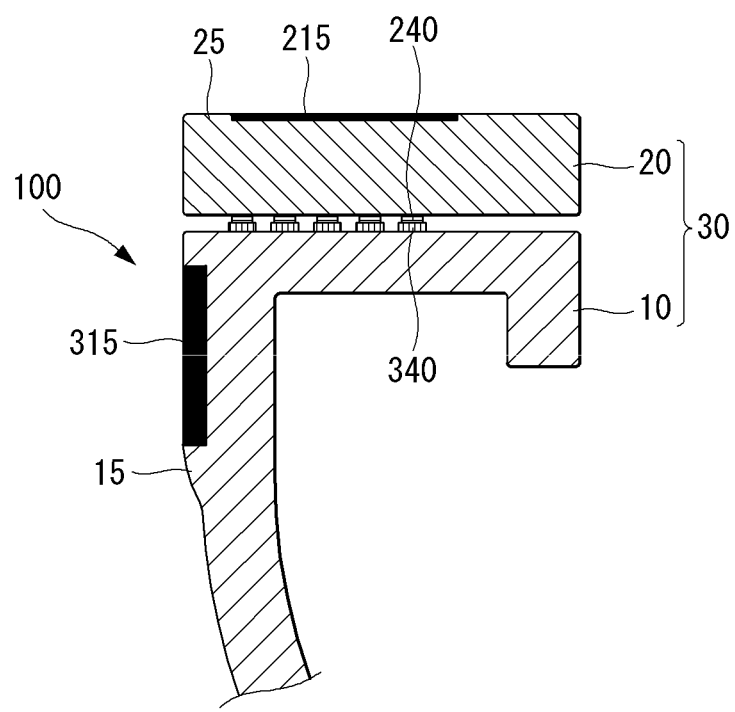
FIG. 22 is a view illustrating an electronic devices according to another embodiment of the present invention.

FIG. 22 is a view illustrating an electronic devices according to another embodiment of the present invention.

As shown in this figure, according to the instant embodiment of the present invention, the electronic device 100 may be integrally formed with the toilet 30. The electronic device 100 may be embedded in the toilet 30. That means, for example, that at least some components of the electronic device 100 may be buried in the seat cover 20 and/or pottery bowl 10.

The first electrode 215 may be positioned in an upper surface 25 of the seat cover 20. The first electrode 215 and the upper surface 25 may be positioned on substantially the same plane. Accordingly, the user's discomfort may be reduced when seated on the seat cover 20.

The second electrode 315 may be positioned in a side surface 15 of the pottery bowl 10.

As the first and second electrodes 215 and 315, along with the seat cover 20 and/or the pottery bowl 10, form a single body, the overall look may be enhanced.

The first and second terminals 240 and 340 may play a role as a pathway to electrically connecting the components embedded in the compensation current generating unit 20 with the components embedded in the pottery bowl 10. The first and second terminals 240 and 340 are positioned between the seat cover 20 and the pottery bowl 10, avoided from being exposed to the outside.

FIG. 23 is a block diagram of a mobile terminal according to an embodiment. Other embodiments, configurations and arrangements may also be provided.

As shown, the mobile terminal 100 may include a wireless communication unit 110 (or radio communication unit), an audio/video (NV) input unit 120, a user input unit 130, a sensing unit 140, an output unit 150, a memory 160, an interface 170, a controller 180, and a power supply 190. The components shown in FIG. 23 may be essential parts and/or a number of components included in the mobile terminal 100 may vary. Components of the mobile terminal 100 may now be described.

The wireless communication unit 110 may include at least one module that enables radio communication between the mobile terminal 100 and a radio communication system or between the mobile terminal 100 and a network in which the mobile terminal 100 is located. For example, the wireless communication unit 110 may include a broadcasting receiving module 111, a mobile communication module 112, a wireless Internet module 113, a short range communication module 114 (or local area communication module), and a location information module 115 (or position information module).

The broadcasting receiving module 111 may receive broadcasting signals and/or broadcasting related information from an external broadcasting management server through a broadcasting channel. The broadcasting channel may include a satellite channel and a terrestrial channel, and the broadcasting management server may be a server that generates and transmits broadcasting signals and/or broadcasting related information or a server that receives previously created broadcasting signals and/or broadcasting related information and transmits the broadcasting signals and/or broadcasting related information to a terminal.

The broadcasting signals may include not only TV broadcasting signals, radio broadcasting signals, and data broadcasting signals but also signals in the form of a combination of a TV broadcasting signal and a radio broadcasting signal. The broadcasting related information may be information on a broadcasting channel, a broadcasting program or a broadcasting service provider, and may be provided even through a mobile communication network. In the latter case, the broadcasting related information may be received by the mobile communication module 112.

The broadcasting related information may exist in various forms. For example, the broadcasting related information may exist in the form of an electronic program guide (EPG) of a digital multimedia broadcasting (DMB) system or in the form of an electronic service guide (ESG) of a digital video broadcast-handheld (DVB-H) system.

The broadcasting receiving module 111 may receive broadcasting signals using various broadcasting systems. More particularly, the broadcasting receiving module 111 may receive digital broadcasting signals using digital broadcasting systems such as a digital multimedia broadcasting-terrestrial (DMB-T) system, a digital multimedia broadcasting-satellite (DMB-S) system, a media forward link only (MediaFLO) system, a DVB-H and integrated services digital broadcast-terrestrial (ISDB-T) systems. The broadcasting receiving module 111 may receive signals from broadcasting systems providing broadcasting signals other than the above-described digital broadcasting systems.

The broadcasting signals and/or broadcasting related information received through the broadcasting receiving module 111 may be stored in the memory 160. The mobile communication module 112 may transmit/receive a radio signal to/from at least one of a base station, an external terminal and a server on a mobile communication network. The radio signal may include a voice call signal, a video telephony call signal or data in various forms according to transmission and reception of text/multimedia messages.

The wireless Internet module 113 may correspond to a module for wireless Internet access and may be included in the mobile terminal 100 or may be externally attached to the mobile terminal 100. Wireless LAN (WLAN or Wi-Fi), wireless broadband (Wibro), world interoperability for microwave access (Wimax), high speed downlink packet access (HSDPA) and so on may be used as a wireless Internet technique.

The short range communication module 114 may correspond to a module for short range communication. Further, Bluetooth®, radio frequency identification (RFID), infrared data association (IrDA), ultra wideband (UWB) and/or Zig-Bee® may be used as a short range communication technique.

The location information module 115 may confirm or obtain a location or a position of the mobile terminal 100. The location information module 115 may obtain position information by using a global navigation satellite system (GNSS). The GNSS is a terminology describing a radio navigation satellite system that revolves around the earth and transmits reference signals to predetermined types of radio navigation receivers such that the radio navigation receivers can determine their positions on the earth's surface or near the earth's surface. The GNSS may include a global positioning system (GPS) of the United States, Galileo of Europe, a global orbiting navigational satellite system (GLONASS) of Russia, COMPASS of China, and a quasi-zenith satellite system (QZSS) of Japan, for example.

A global positioning system (GPS) module is a representative example of the location information module 115. The GPS module may calculate information on distances between one point or object and at least three satellites and information on a time when distance information is measured and apply trigonometry to the obtained distance information to obtain three-dimensional position information on the point or object according to latitude, longitude and altitude at a predetermined time.

A method of calculating position and time information using three satellites and correcting the calculated position and time information using another satellite may also be used. Additionally, the GPS module may continuously calculate a current position in real time and calculate velocity information using the location or position information.

The A/V input unit 120 may input (or receive) an audio signal and/or a video signal. The A/V input unit 120 may include a camera 121 and a microphone 122. The camera 121 may process image frames of still images or moving images obtained by an image sensor in a video telephony mode or a photographing mode. The processed image frames may be displayed on a display 151, which may be a touch screen.

The image frames processed by the camera 121 may be stored in the memory 160 or may be transmitted to an external device through the wireless communication unit 110. The mobile terminal 100 may also include at least two cameras 121.

The microphone 122 may receive an external audio signal in a call mode, a recording mode and/or a speech recognition mode, and the microphone 122 may process the received audio signal into electric audio data. The audio data may then be converted into a form that can be transmitted to a mobile communication base station through the mobile communication module 112 and output in the call mode. The microphone 122 may employ various noise removal algorithms (or noise canceling algorithm) for removing or reducing noise generated when the external audio signal is received.

The user input unit 130 may receive input data for controlling operation of the mobile terminal 100 from a user. The user input unit 130 may include a keypad, a dome switch, a touch pad (constant voltage/capacitance), a jog wheel, a jog switch and/or so on.

The sensing unit 140 may sense a current state of the mobile terminal 100, such as an open/close state of the mobile terminal 100, a position of the mobile terminal 100, whether a user touches the mobile terminal 100, a direction of the mobile terminal 100, and acceleration/deceleration of the mobile terminal 100, and the sensing unit 140 may generate a sensing signal for controlling operation of the mobile terminal 100. For example, in an example of a slide phone, the sensing unit 140 may sense whether the slide phone is opened or closed. Further, the sensing unit 140 may sense whether the power supply 190 supplies power and/or whether the interface 170 is connected to an external device. The sensing unit 140 may also include a proximity sensor 141. The sensing unit 140 may sense a motion of the mobile terminal 100.

The output unit 150 may generate visual, auditory and/or tactile output, and the output unit 150 may include the display 151, an audio output module 152, an alarm 153 and a haptic module 154. The display 151 may display information processed by the mobile terminal 100. The display 151 may display a user interface (UI) and/or a graphic user interface (GUI) related to a telephone call when the mobile terminal 100 is in the call mode. The display 151 may also display a captured and/or received image, a UI or a GUI when the mobile terminal 100 is in the video telephony mode or the photographing mode.

The display 151 may include at least one of a liquid crystal display, a thin film transistor liquid crystal display, an organic light-emitting diode display, a flexible display and/or a three-dimensional display. The display 151 may be of a transparent type or a light transmissive type. That is, the display 151 may include a transparent display.

The transparent display may be a transparent liquid crystal display. A rear structure of the display 151 may also be of a light transmissive type. Accordingly, a user may see an object located behind the body (of the mobile terminal 100) through the transparent area of the body of the mobile terminal 100 that is occupied by the display 151.

The mobile terminal 100 may also include at least two displays 151. For example, the mobile terminal 100 may include a plurality of displays 151 that are arranged on a single face at a predetermined distance or integrated displays. The plurality of displays 151 may also be arranged on different sides.

When the display 151 and a sensor sensing touch (hereafter referred to as a touch sensor) form a layered structure that is referred to as a touch screen, the display 151 may be used as an input device in addition to an output device. The touch sensor may be in the form of a touch film, a touch sheet, and/or a touch pad, for example.

The touch sensor may convert a variation in pressure applied to a specific portion of the display 151 or a variation in capacitance generated at a specific portion of the display 151 into an electric input signal. The touch sensor may sense pressure of touch as well as position and area of the touch.

When the user applies a touch input to the touch sensor, a signal corresponding to the touch input may be transmitted to a touch controller. The touch controller may then process the signal and transmit data corresponding to the processed signal to the controller 180. Accordingly, the controller 180 may detect a touched portion of the display 151.

The proximity sensor 141 (of the sensing unit 140) may be located in an internal region of the mobile terminal 100, surrounded by the touch screen, and/or near the touch screen. The proximity sensor 141 may sense an object approaching a predetermined sensing face or an object located near the proximity sensor 141 using an electromagnetic force or infrared rays without having mechanical contact. The proximity sensor 141 may have a lifetime longer than a contact sensor and may thus have a wide application in the mobile terminal 100.

The proximity sensor 141 may include a transmission type photo-electric sensor, a direct reflection type photo-electric sensor, a mirror reflection type photo-electric sensor, a high-frequency oscillating proximity sensor, a capacitive proximity sensor, a magnetic proximity sensor, and/or an infrared proximity sensor. A capacitive touch screen may be constructed such that proximity of a pointer is detected through a variation in an electric field according to the proximity of the pointer. The touch screen (touch sensor) may be classified as a proximity sensor 141.

For ease of explanation, an action of the pointer approaching the touch screen without actually touching the touch screen may be referred to as a proximity touch and an action of bringing the pointer into contact with the touch screen may be referred to as a contact touch. The proximity touch point of the pointer on the touch screen may correspond to a point of the touch screen at which the pointer is perpendicular to the touch screen.

The proximity sensor 141 may sense the proximity touch and a proximity touch pattern (e.g., a proximity touch distance, a proximity touch direction, a proximity touch velocity, a proximity touch time, a proximity touch position, a proximity touch moving state, etc.). Information corresponding to the sensed proximity touch action and proximity touch pattern may then be displayed on the touch screen.

The audio output module 152 may output audio data received from the wireless communication unit 110 or stored in the memory 160 in a call signal receiving mode, a telephone call mode or a recording mode, a speech recognition mode and a broadcasting receiving mode. The audio output module 152 may output audio signals related to functions, such as a call signal incoming tone and a message incoming tone, performed in the mobile terminal 100. The audio output module 152 may include a receiver, a speaker, a buzzer, and/or the like. The audio output module 152 may output sounds through an earphone jack. The user may hear the sounds by connecting an earphone to the earphone jack.

The alarm 153 may output a signal for indicating generation of an event of the mobile terminal 100. For example, an alarm may be generated when receiving a call signal, receiving a message, inputting a key signal, and/or inputting a touch. The alarm 153 may also output signals in forms different from video signals or audio signals, for example, a signal for indicating generation of an event through vibration. The video signals and/or the audio signals may also be output through the display 151 or the audio output module 152.

The haptic module 154 may generate various haptic effects that the user can feel. One example of the haptic effects is vibration. An intensity and/or pattern of vibration generated by the haptic module 154 may also be controlled. For example, different vibrations may be combined and output or may be sequentially output.

The haptic module 154 may generate a variety of haptic effects including an effect of stimulus according to an arrangement of pins vertically moving against a contact skin surface, an effect of stimulus according to a jet force or sucking force of air through a jet hole or a sucking hole, an effect of stimulus of rubbing the skin, an effect of stimulus according to contact of an electrode, an effect of stimulus using an electrostatic force, and an effect according to a reproduction of cold and warmth using an element capable of absorbing or radiating heat in addition to vibrations.

The haptic module 154 may not only transmit haptic effects through direct contact but may also allow the user to feel haptic effects through a kinesthetic sense of the user's fingers or arms. The mobile terminal 100 may also include a plurality of haptic modules 154.

The memory 160 may store a program for operations of the controller 180 and/or temporarily store input/output data such as a phone book, messages, still images, and/or moving images. The memory 160 may also store data about vibrations and sounds in various patterns that are output from when a touch input is applied to the touch screen.

The memory 160 may include at least a flash memory, a hard disk type memory, a multimedia card micro type memory, a card type memory, such as SD or XD memory, a random access memory (RAM), a static RAM (SRAM), a read-only memory (ROM), an electrically erasable programmable ROM (EEPROM), a programmable ROM (PROM) magnetic memory, a magnetic disk and/or an optical disk. The mobile terminal 100 may also operate in relation to a web storage that performs a storing function of the memory 160 on the Internet.

The interface 170 may serve as a path to external devices connected to the mobile terminal 100. The interface 170 may receive data from the external devices or power and transmit the data or power to internal components of the mobile terminal 100 or transmit data of the mobile terminal 100 to the external devices. For example, the interface 170 may include a wired/wireless headset port, an external charger port, a wired/wireless data port, a memory card port, a port for connecting a device having a user identification module, an audio I/O port, a video I/O port, and/or an earphone port.

The interface 170 may also interface with a user identification module that is a chip that stores information for authenticating authority to use the mobile terminal 100. For example, the user identification module may be a user identify module (UIM), a subscriber identify module (SIM) and/or a universal subscriber identify module (USIM). An identification device (including the user identification module) may also be manufactured in the form of a smart card. Accordingly, the identification device may be connected to the mobile terminal 100 through a port of the interface 170.

The interface 170 may also be a path through which power from an external cradle is provided to the mobile terminal 100 when the mobile terminal 100 is connected to the external cradle or a path through which various command signals input by the user through the cradle are transmitted to the mobile terminal 100. The various command signals or power input from the cradle may be used as signals for confirming whether the mobile terminal 100 is correctly set in the cradle.

The controller 180 may control overall operations of the mobile terminal 100. For example, the controller 180 may perform control and processing for voice communication, data communication and/or video telephony. The controller 180 may also include a multimedia module 181 for playing multimedia. The multimedia module 181 may be included in the controller 180 or may be separated from the controller 180.

The controller 180 may perform a pattern recognition process capable of recognizing handwriting input or picture-drawing input applied to the touch screen as characters or images. The power supply 190 may receive external power and internal power and provide power required for operations of the components of the mobile terminal 100 under control of the controller 180.

According to hardware implementation, embodiments may be implemented using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, and/or electrical units for executing functions. Embodiments may be implemented by the controller 180.

According to software implementation, embodiments such as procedures or functions may be implemented with a separate software module that executes at least one function or operation. Software codes may be implemented according to a software application written in an appropriate software language. The software codes may be stored in the memory 160 and executed by the controller 180.

The above-described method of controlling the mobile terminal may be written as computer programs and may be implemented in digital microprocessors that execute the programs using a computer readable recording medium. The method of controlling the mobile terminal may be executed through software. The software may include code segments that perform required tasks. Programs or code segments may also be stored in a processor readable medium or may be transmitted according to a computer data signal combined with a carrier through a transmission medium or communication network.

The computer readable recording medium may be any data storage device that can store data that can be thereafter read by a computer system. Examples of the computer readable recording medium may include read-only memory (ROM), random-access memory (RAM), CD-ROMs, DVD±ROM, DVD-RAM, magnetic tapes, floppy disks, optical data storage devices. The computer readable recording medium may also be distributed over network coupled computer systems so that the computer readable code is stored and executed in a distribution fashion.

A mobile terminal may include a first touch screen configured to display a first object, a second touch screen configured to display a second object, and a controller configured to receive a first touch input applied to the first object and to link the first object to a function corresponding to the second object when receiving a second touch input applied to the second object while the first touch input is maintained.

A method may be provided of controlling a mobile terminal that includes displaying a first object on the first touch screen, displaying a second object on the second touch screen, receiving a first touch input applied to the first object, and linking the first object to a function corresponding to the second object when a second touch input applied to the second object is received while the first touch input is maintained.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:
1. An electronic device, comprising: a body;
a plurality of electrodes exposed to a surface of the body and configured to make contact with at least two portions of a user's body;
a controller configured to apply a current to at least one of the plurality of electrodes to obtain a bio signal of the user's body, and
a coupler coupled to the body,
wherein the coupler comprises a cover assembly that is detachably coupled to a seat cover and a bowl assembly that is detachably coupled to a pottery bowl,
wherein the cover assembly is slidable and configured to slide in and out of a side surface of the seat cover,
wherein the bowl assembly comprises:
a first upper plate;
a second upper plate positioned on substantially a same plane as the first upper plate; and
a third upper plate that is slidable and configured to be slidingly inserted into an inside of at least one of the first upper plate and the second upper plate in order to adjust an interval between the first upper plate and the second upper plate depending on a shape of the pottery bowl.

2. The electronic device of claim 1, wherein the cover assembly and the bowl assembly each include at least one electrode of the plurality of electrodes configured to contact the user's body to apply an electrical signal.

3. The electronic device of claim 2, wherein the at least one electrode includes a first electrode positioned in an upper surface of the cover assembly adapted to contact a thigh of the user and a second electrode positioned in an outside surface of the bowl assembly adapted to contact a finger of the user.

4. The electronic device of claim 3, wherein the controller is configured to, after applying the electrical signal to at least one of the first and second electrodes, obtain bio information of the user based on a change in the electrical signal sensed through at least another one of the first and second electrodes.

5. The electronic device of claim 1, wherein the body includes a camera sensor positioned on the body and adapted to face towards an inside of the pottery bowl of a toilet to image at least one of a color and shape of excreta discharged from the user.

\* \* \* \* \*